(12) United States Patent
Xu

(10) Patent No.: US 9,416,159 B2
(45) Date of Patent: Aug. 16, 2016

(54) METHOD OF PRODUCING A POSITIVE INOTROPIC EFFECT USING AN ANTIBODY THAT BINDS SODIUM POTASSIUM ATPASE

(71) Applicant: Kai Yuan Xu, Cockeysville, MD (US)

(72) Inventor: Kai Yuan Xu, Cockeysville, MD (US)

( * ) Notice: Subject to any disclaimer, the term of this patent is extended or adjusted under 35 U.S.C. 154(b) by 154 days.

(21) Appl. No.: 13/856,818

(22) Filed: Apr. 4, 2013

(65) Prior Publication Data

US 2013/0345407 A1  Dec. 26, 2013

Related U.S. Application Data

(62) Division of application No. 11/910,943, filed as application No. PCT/US2006/012912 on Apr. 7, 2006, now Pat. No. 8,435,519.

(60) Provisional application No. 60/669,479, filed on Apr. 8, 2005.

(51) Int. Cl.
| | |
|---|---|
| *A61K 39/00* | (2006.01) |
| *C07K 7/08* | (2006.01) |
| *C07K 16/40* | (2006.01) |
| *C12N 9/14* | (2006.01) |

(52) U.S. Cl.
CPC ............... *C07K 7/08* (2013.01); *A61K 39/0005* (2013.01); *C07K 16/40* (2013.01); *C12N 9/14* (2013.01); *A61K 39/00* (2013.01); *A61K 2039/505* (2013.01); *C07K 2317/75* (2013.01); *G01N 2333/914* (2013.01); *G01N 2500/04* (2013.01); *G01N 2800/325* (2013.01)

(58) Field of Classification Search
None
See application file for complete search history.

(56) References Cited

U.S. PATENT DOCUMENTS

2012/0020956 A1 * 1/2012 Xu ..................... A61K 39/0005
424/133.1

OTHER PUBLICATIONS

Isidro-Llobet et al. (PNAS 2011, 108:6793-6798).*

* cited by examiner

*Primary Examiner* — Sharon Wen

(57) ABSTRACT

Activation sites on the alpha subunit of sodium potassium ATPase have been discovered. It has also been discovered that certain antibodies that bind to the alpha subunit of sodium potassium ATPase dramatically increase enzyme activity. There has never before been a report of precise activation sites or drug interaction sites for sodium potassium ATPase. Certain methods have also been discovered for treating or preventing diseases associated with low sodium potassium ATPase activity by administering antibodies, antibody fragments and small molecules that bind to the activation sites on the alpha subunit of sodium potassium ATPase.

6 Claims, 19 Drawing Sheets

FIG. 1A

| | | |
|---|---|---|
| Rat | α1 | $^{897}$DVEDSYGQQWTYEQR$^{911}$ |
| Human | α1 | $^{897}$DVEDSYGQQWTYEQR$^{911}$ |
| Dog | α1 | $^{895}$DVEDSYGQQWTYEQR$^{909}$ |
| Sheep | α1 | $^{895}$DVEDSYGQQWTYEQR$^{909}$ |
| Pig | α1 | $^{895}$DVEDSYGQQWTYEQR$^{909}$ |
| Rat | α2 | $^{894}$DLEDSYGQEWTYEQR$^{908}$ |
| Human | α2 | $^{894}$DLEDSYGQEWTYEQR$^{908}$ |
| Rat | α3 | $^{887}$DLEDSYGQQWTYEQR$^{901}$ |
| Human | α3 | $^{894}$DLEDSYGQQWTYEQR$^{901}$ |

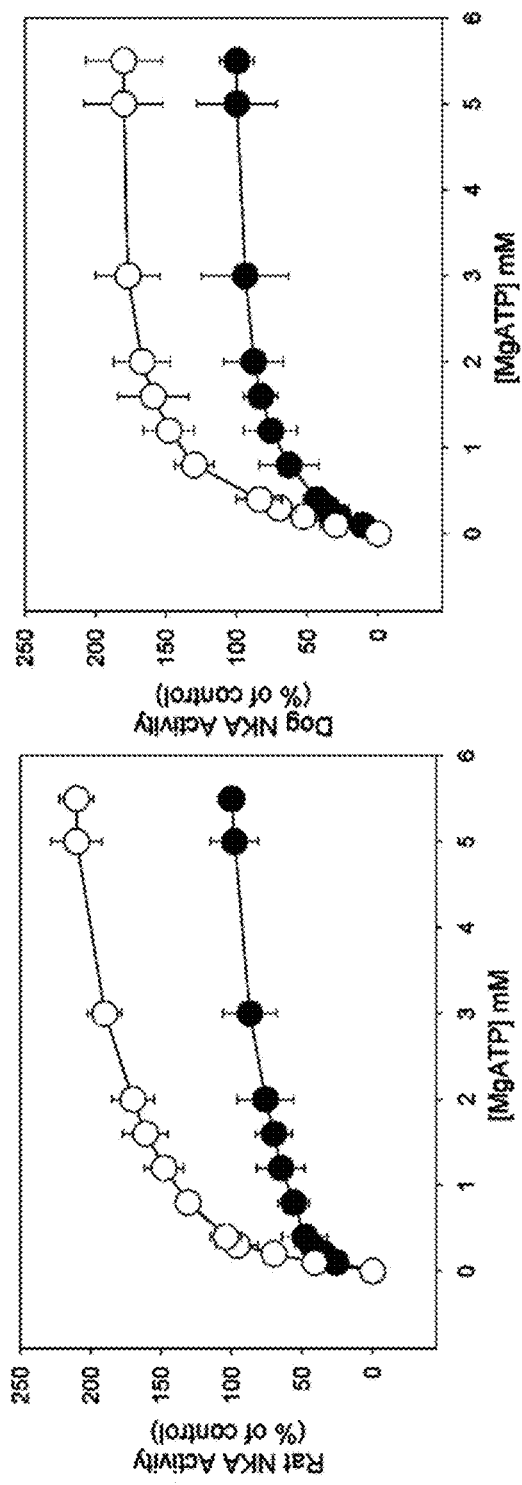

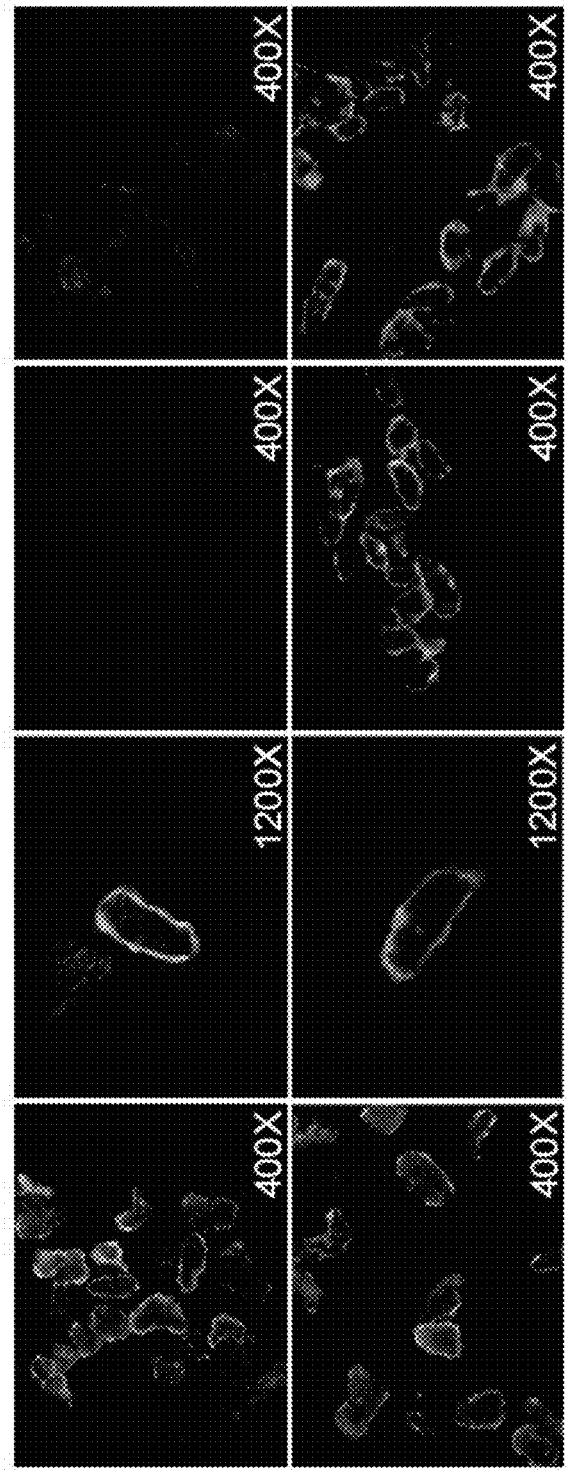

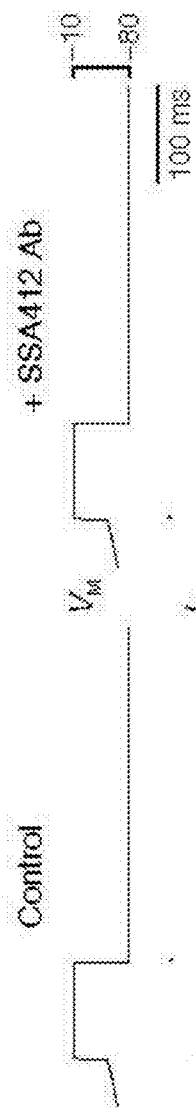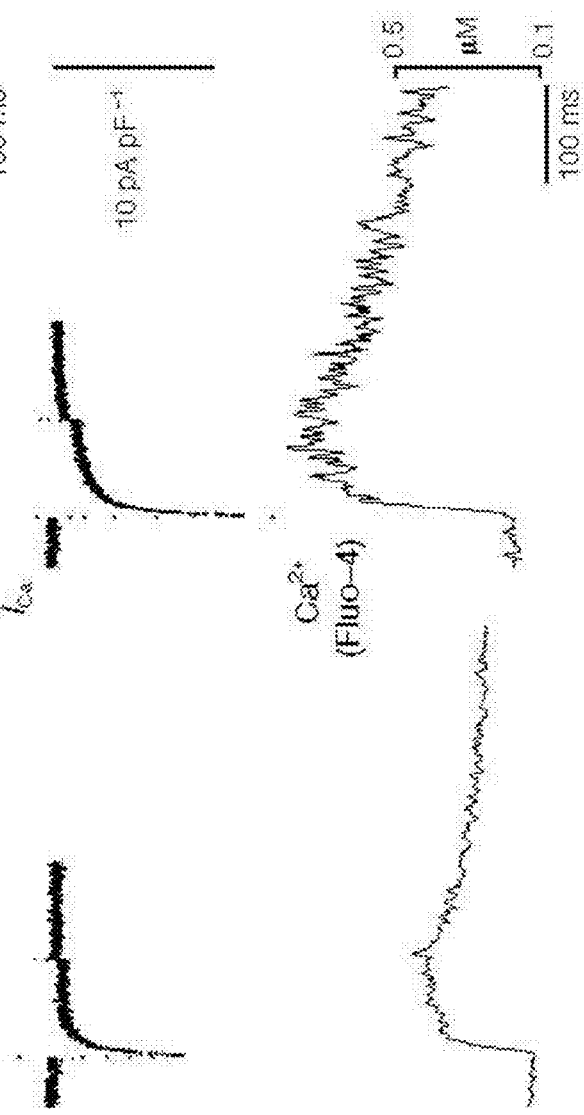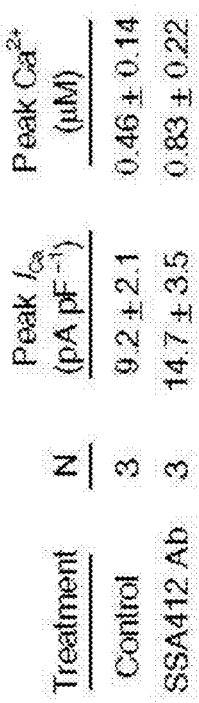
FIG. 9A  FIG. 9B  FIG. 9C  FIG. 9D

```
                              SEQUENCE LISTING

<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 1

Lys Arg Gln Pro Arg Asn Pro Lys Thr Asp Lys Leu Val Asn Glu
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Activation site of the (NA+K)-ATPase
```

```
<400> SEQUENCE: 2

Val Pro Ala Ser Leu Ala Tyr Glu Gln Ala Glu Ser Asp
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Activation site of the (Na+K)-ATPase

<400> SEQUENCE: 3

Arg Ser Ala Thr Glu Glu Glu Pro Pro Asn Asp Asp
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 4

His Leu Leu Gly Ile Arg Glu Thr Trp Asp Asp Arg Trp Ile Asn
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 5

Asp Val Glu Asp Ser Tyr Gly Gln Gln Trp Thr Tyr Glu Gln Arg
1               5                   10                  15
```

METHOD OF PRODUCING A POSITIVE INOTROPIC EFFECT USING AN ANTIBODY THAT BINDS SODIUM POTASSIUM ATPASE

CROSS-REFERENCE TO RELATED APPLICATIONS

This Divisional application claims benefit of Provisional Application. 60/669,479, filed Apr. 8, 2005, the entire contents of which are hereby incorporated by reference as if fully set forth herein, under 35 U.S.C. §119(e). Allowed original parent application is now U.S. Pat. No. 8,435,519.

STATEMENT OF GOVERNMENTAL INTEREST

Parts of this invention were made with Government support under Contract No. HL52175 awarded by NIH/NHLBI. The Government may have certain rights in the invention.

BACKGROUND OF THE INVENTION

1. Field of the Invention

The present invention relates to antibodies, pharmaceutical compositions and methods for increasing all isoforms of sodium potassium ATPase activity in a cell, tissue, organ, or bodily fluid. It also relates to the use of the antibodies and pharmaceutical compositions to treat or prevent diseases associated with low NKA activity in an animal.

2. Description of the Related Art

Sodium potassium ATPase (hereafter referred to as "NKA") [1] is an integral membrane protein that couples the hydrolysis of ATP to the vectorial transport of $Na^+$ ions and $K^+$ ions across the plasma membrane of all animal cells [2]. The overall stoichiometry of the reaction is three $Na^+$ ions transported out of the cell and two $K^+$ ions into the cell for each ATP hydrolyzed. It has been demonstrated that intact NKA is composed of two subunits and only the α-subunit (~113 kDa) is responsible for the catalytic activity of the enzyme. The smaller β-subunit (~35 kDa glycoprotein) is necessary for the folding of the complex [3]. Recent transmembrane investigations have suggested that the catalytic α-subunit traverses the membrane ten times and both the N- and C-terminals of the α-subunit are located on the cytoplasmic side [4, 5]. The β-subunit contains one hydrophobic region and only the N-terminal is located on the cytoplasmic side [5, 6]. Several isoforms of both α- and β-subunits have been identified [7]. There are two α isoforms (α1 and α2) on NKA in rodent heart[8, 9] and three α isoforms (α1, α2, and α3) in human heart [10, 11]. All isoforms of NKA share the same catalytic function.

Although extensive studies have been made towards understanding the structure/function relationship of NKA and its central role in biology and medicine, little is known about the activation of NKA and its biological influences. Enzymatic activity of NKA is essential to living cells and continuity of life. However, in certain diseases including heart diseases, liver diseases, lung diseases, Alzheimer's disease, nervous system diseases, intestinal diseases, cataracts and blood diseases, NKA activity is depressed. In the fifty years since the discovery of NKA, there have been no drugs or compounds identified that selectively activate NKA activity.

The past approaches described in this section could be pursued, but are not necessarily approaches that have been previously conceived or pursued. Therefore, unless otherwise indicated herein, the approaches described in this section are not to be considered prior art to the claims in this application merely due to the presence of these approaches in this background section.

SUMMARY OF THE INVENTION

Specific drug interaction sites on NKA are provided for increasing enzyme catalytic activity for prevention and treatment of various diseases associated with low expression and activity. There has never before been a report of precise activation sites or drug interaction sites on NKA. Certain embodiments of the invention are therefore directed to an NKA activation site in the alpha subunit that is selected from the group comprising the amino acid sequences DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and variants, derivatives or fragments thereof. Certain embodiments of the invention are also directed to methods and compounds that interact with these activation sites to treat or prevent diseases.

In one set of embodiments the invention is directed to pharmaceutical compositions that increase NKA in a cell or bodily fluid, such as hepatocytes, kidney cells, red blood cells, endothelial cells, lung cells, nerve cells, lens cells, brain cells, muscle cells, and cardiac myocytes. These compositions contain an antibody, antibody fragment or small molecule that binds to an activation site on the alpha subunit of any isoform of NKA, which activation site includes sites with the amino acid sequences DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and variants or fragments thereof. In certain embodiments the antibody is one or more of the following: SSA78, SSA95, SSA97, SSA401 and SSA412. Some embodiments are directed to administering these pharmaceutical compositions for treating or preventing a disease associated with low NKA expression or activity in an animal cell or bodily fluid, especially diseases like diabetes, lung diseases, liver diseases, hypertension, urinary tract diseases, hemorrhagic shock, gastrointestinal diseases including colitis, cataracts, obesity, cancer, kidney disease, hypertension, Alzheimer's disease, eye disease, heart disease, aging and diseases of the nervous system.

One embodiment is directed to a newly discovered isolated antibody SSA401 or a fragment thereof that recognizes and binds to an epitope in the alpha subunit of any isoform of NKA having the amino acid sequence HLLGIRETWDDRWIN (SEQ ID:4) or to a fragment, derivative or variant thereof. Such antibodies increase myocyte intracellular diastolic and systolic calcium and exert a positive inotropic effect in cardiac myocytes. Thus certain embodiments are directed to the use of such antibodies or antibody fragments to treat or prevent heart disease or muscle contractile disorders. All of the antibodies described and used in the present invention can be exogenous or endogenous, polyclonal, monoclonal or humanized, and they can be administered systemically or locally.

Some embodiments are directed to methods for increasing the activity of any isoform of NKA in an animal cell or bodily fluid, by administering to the animal an antibody, an antibody fragment or a small molecule that recognizes and binds to an epitope in the alpha subunit of any isoform of NKA, which epitope has an amino acid sequence that is a member selected from the group comprising DVEDSYGQQWTYEQR (SEQ ID: 5), RSATEEEPPNDD (SEQ ID: 3), KRQPRNPKTD- KLVNE (SEQ ID: 1), VPAISLAYEQAESD (SEQ ID: 2) and HLLGIRETWDDRWIN (SEQ ID: 4), and fragments, derivatives and variants thereof.

Certain other embodiments are directed to methods for treating or preventing a disease in an animal that is associated with low expression or activity of any isoform of NKA in a cell or bodily fluid, by administering to the animal one or more peptides representing antigenic sites or epitopes on NKA from the group comprising DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and fragments, derivatives and variants thereof, which peptides are administered in an amount that stimulates the animal's immune system to produce (endogenous) antibodies that recognize and bind to the respective peptide epitopes (or antigenic sites) on the alpha subunit of the NKA, thereby increasing ATPase activity in the cell or bodily fluid. Some embodiments are directed to methods for increasing the activity of any isoform of NKA in an animal cell or bodily fluid or to treating or preventing a disease associated with low expression or activity of NKA, by administering a vector that carries a gene encoding one or more peptides selected from the activation sites in the group comprising DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and fragments, derivatives and variants thereof. In some embodiments the vector has tissue specific promoters.

Still other embodiments are directed to a purified peptide that includes the amino acid sequence HLLGIRETWDDRWIN (SEQ ID: 4) or fragments, derivatives and variants thereof, and to antibodies, antibody fragments and small molecules that recognize and bind to this epitope on any isoform of NKA in any cell or tissue or bodily fluid. Some embodiments are directed to methods whereby the administration of such to antibodies, antibody fragments and small molecules increases cardiac contraction and diastolic and systolic calcium, and thus can be used to treat or prevent heart disease and contractile disorders.

One embodiment is directed to a method for determining if a compound activates NKA. The method has the steps of a) identifying an assay for quantifying NKA activity, b) using the assay, determining a baseline level of NKA activity in a control sample, c) in a separate binding assay, incubating the compound with a peptide that defines an antigenic site on the ATPase which peptide has an amino acid sequence selected from the group comprising DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and fragments, derivatives or variants thereof under conditions that permit the compound to bind to the peptide, d) determining whether the compound binds to the peptide in step c), e) if the compound binds to the peptide, then forming a mixture of the compound and NKA under conditions that permit the compound to bind to the ATPase, f) using the assay of step a) and under the same conditions as in step b) determining the level of ATPase activity in the mixture, and g) if the level of ATPase activity in the mixture is increased above the baseline level in the control sample determined in step b), then concluding that the compound activates NKA.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A shows that the primary amino acid sequence of the D-R region (SEQ ID: 5) (SSA412 binding site) is identical for the α1-subunits of rat, human, dog, sheep, and pig. The D-R region (SEQ ID: 5) is also highly conserved in α2 (87%) and α3 (93%) NKA isoforms. These conserved sequences in α2 and α3 are isoforms of SEQ ID: 5. FIG. 1B-A: 30 μg of purified dog kidney NKA, FIG. 1B-B: 10 μg of immunoprecipitates, FIG. 1B-C: cell lysates. For Western blots: FIG. 1B-D: dog kidney NKA stained with SSA78 as positive control, FIG. 1B-E: 10 μg immunoprecipitates stained with SSA412, FIG. 1B-F: 10 μg immunoprecipitates stained with SERCA2 as negative control, FIG. 1B-G 10 μg immunoprecipitates stained with secondary antibody as background control, FIG. 1B-H: 10 μg immunoprecipitates stained with anti-α2 antibody, FIG. 1B-I: 10 μg immunoprecipitates stained with anti-α3 antibody, FIG. 1B-J: 10 μg rat brain immunoprecipitates stained with anti-α3 antibody, FIG. 1B-K: rat cardiac SR vesicles stained with SERCA2, FIG. 1B-L: SR vesicles stained with SSA412. The 55,000 Da band in Western blots FIGS. 1B-E-J shows the denatured heavy domains of IgG. SSA412 recognizes the α-subunit of three isoforms of NKA, but not SR $Ca^{2+}$-ATPase. Each of the data represents one of six similar experiments.

FIG. 3C and FIG. 3D show that in the presence of different concentrations of MgATP, with or without 0.5 μM of SSA412, the Km values for both rat (FIG. 3C) and dog (FIG. 3D) NKA decreased 16 and 15% respectively, while the enzyme turnover rates increased. FIG. 3C: For rat NKA control sample: $Km_{MgATP}$=0.50 mM is indicated by closed circles; open circles indicates rat NKA with SSA412: $Km_{MgATP}$=0.42 mM. FIG. 3D: For dog NKA control: $Km_{MgATP}$=0.53 mM is indicated by closed circles; open circles indicates dog NKA with SSA412: $Km_{MgATP}$=0.45 mM.

(0.25 µM), and (FIG. 4B) before and after administration of SSA412+0.5 mM peptide blocker.

FIG. 5 shows the immunofluorescent staining of SSA412 in rat cardiac myocytes with SSA412 and without ouabain: FIG. 5A: a group of cells at a magnification of 400×, FIG. 5B: a single myocyte at 1200×, FIG. 5C: with SSA412 and peptide blocker, FIG. 5D: secondary antibody control. With both ouabain and SSA412: FIG. 5E: a group of cells with 5 mM ouabain at a magnification of 400×, FIG. 5F: a single cell with 5 mM ouabain at 1200×, FIG. 5G: cells with 10 mM ouabain, FIG. 5H: cells with 20 mM ouabain. The results show that the D-R region (SSA412 binding site) is not an ouabain or digitalis interaction site. Each of these data represents one of 12 similar immunofluorescent stainings.

FIG. 6A: control, FIG. 6B: control+2 mM nonradioactive ouabain, FIG. 6C: with 1 µM SSA412 SSA412, FIG. 6D: SSA412+2 mM nonradioactive ouabain, FIG. 6E: with 1 µM SSA78, FIG. 6F: SSA78+2 mM nonradioactive ouabain. Specific ouabain binding is presented as the difference between [$^3$H]ouabain binding in the presence and absence of nonradioactive ouabain. The results represent mean values of 9 independent experiments each.

FIG. 7A: the control NKA activity level, FIG. 7B: with SSA95, FIG. 7C: with SSA95+peptide blocker PB95 that has the amino acid sequence KRQPRNPKTDKLVNE (SEQ ID: 1), FIG. 7D: with SSA78, FIG. 7E: with SSA78+PB78 that has the amino acid sequence the RSATEEEPPNDD (SEQ ID: 3), FIG. 7F: with SSA97, and FIG. 7G: with SSA97+PB97 that has the amino acid sequence VPAISLAYEQAESD (SEQ ID: 2).

FIG. 9 shows the mechanism of activation of NKA-induced increasing of $Ca^{2+}$ transients. Rat neonatal ventricular myocytes and 'whole-cell' patch-clamp were used for the investigation. Myoplasmic $Ca^{2+}$ was determined from simultaneous confocal optical recording of fluo-4 fluorescence. The left-hand column represents a control myocyte, while the right-hand column shows results from a myocyte previously exposed to SSA412 antibody (1.0 µM). FIG. 9A: the voltage pulse protocol, $V_M$. A ramp preceded each test pulse (−10 mV, 100 ms) in order to suppress $Na^+$ and T-type $Ca^{2+}$ currents. FIG. 9B: LTCC currents ($I_{Ca}$), corrected for linear capacitance and leak using a P/4 protocol. FIG. 9C: myoplasmic $Ca^{2+}$ during and after the test pulse. Panel shows the myoplasmic $Ca^{2+}$ as determined from confocal line-scan (x vs. t) images. FIG. 9D: averaged results of peak $I_{Ca}$ and peak myoplasmic $Ca^{2+}$ elevation in each group. The results show that the binding of SSA412 to NKA activates LTCC activity, which simultaneously triggers SR calcium release. The data suggest that 1) SR calcium is involved in the mechanistic pathways of activation of NKA-mediated cardiac contraction, 2) LTCC-regulated $Ca^{2+}$-induced $Ca^{2+}$-release (CICR) may account for how activation of NKA triggers the positive inotropic effect. Values represent the mean (±SEM). Values represent the mean (±SEM).

DETAILED DESCRIPTION

Figure 1B:
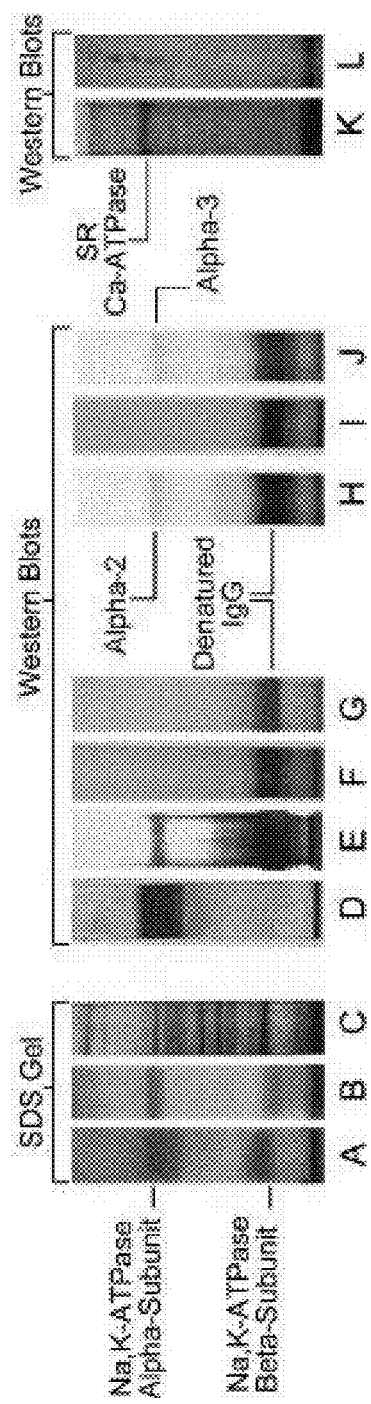
FIG. 1B shows the results of immunoprecipitation followed by electrophoresis and Western blotting of whole rat heart cell lysates. For SDS gel.

In the following description, for the purposes of explanation, numerous specific details are set forth in order to provide a thorough understanding of the present invention. It will be apparent, however, to one skilled in the art that the present invention may be practiced without these specific details. Definitions for certain terms used herein are set forth below at the end of the detailed description.

It has been discovered that certain antibodies that bind to specific sites on the alpha subunit of NKA dramatically increase NKA activity. "NKA" and "sodium potassium ATPase" are used interchangeably herein. These specific sites are called activation sites. There has never before been a report of precise activation sites or drug interaction sites on NKA. We have discovered that the amino acid sequences DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), are activation sites on the alpha subunit of NKA. Certain embodiments of the invention are therefore directed to these activation sites and to fragments, derivatives or variants thereof. Antibodies and fragments thereof that bind to the alpha subunit thereby increasing NKA activity are collectively referred to herein as "NKA activity-increasing antibodies." The NKA-activity-increasing antibodies all bind to various epitopes or antigenic determinants defined by the above amino acid sequences or fragments, derivatives and variants thereof on any isoforms of NKA. They include:

1) Those that bind to the amino acid sequence DVEDSYGQQWTYEQR (SEQ ID: 5) in the H7-H8 domain (including the SS412 antibody referred to also as the KX-1 antibody), or to fragments, derivatives and variants thereof.

2) Those that bind to the amino acid sequence RSATEEEPPNDD (SEQ ID: 3) in the H1-H2 domain (including the SSA78 antibody also referred to as the Jianye 2 antibody), or to fragments, derivatives and variants thereof.

3) Those that bind to the amino acid sequence KRQPRNPKTDKLVNE (SEQ ID: 1) in the H5-H6 domain (including the SSA95 antibody also referred to as the Jianye antibody), or to fragments, derivatives and variants thereof.

4) Those that bind to the amino acid sequence VPAISLAYEQAESD (SEQ ID: 2) in the H5-H6 domain (including the SSA97 antibody also referred to as the Zulan antibody), or to fragments, derivatives and variants thereof.

5) Those that bind to the newly discovered amino acid sequence HLLGIRETWDDRWIN (SEQ ID: 4) in the H7-H8 domain of NKA adjacent to the D-R region (including the newly discovered SSA401 or KX-2 antibody), or to fragments, derivatives and variants thereof. The HLLGIRETWDDRWIN (SEQ ID: 4) site on NKA is a newly discovered site capable of causing both NKA activation and a positive ionotropic effect on cardiac myocytes.

All isoforms of the alpha subunit of NKA share the same enzymatic function. Therefore any antibody or antibody fragment or small molecule that binds to any of the five activation sites described above or to a fragment, derivative or variant of the activation site on any of the isoforms of NKA will increase the enzymatic activity. Certain embodiments of the present invention are directed to pharmaceutical compositions that increase NKA activity in an animal cell or bodily fluid, which compositions include any antibody, antibody fragment or small molecule that binds to an activation site on NKA, which activation sites include DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and variants or fragments thereof. Other embodiments are directed to methods of increasing NKA activity in an animal cell or bodily fluid, by administering to the animal an NKA activity-increasing amount of one or more of the five NKA activity-increasing antibodies listed above. Antibodies useful in the present invention can be monoclonal or polyclonal, and may be humanized. Animal cells include mammalian cells, preferably human cells, and include but are not limited to liver cells, heart cells, kidney cells, nerve cells, red blood cells, endothelial cells, brain tissue, lung cells, lens cells and cells in the gastrointestinal tract. Any cell that expresses NKA can be contacted with the NKA activity-increasing antibodies to increase NKA activity in vivo or in vitro. Antibodies can be administered to an animal in any way known in the art, including locally and systemically.

The invention also includes increasing NKA activity in an animal cell by administering a vaccine that includes one or more peptides selected from a group of peptides having the amino acid sequences DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and variants or fragments thereof. These peptides represent antigenic determinants or epitopes on the alpha 1-subunit of NKA. The peptide vaccines stimulate the host immune system to generate antibodies against the respective one or more peptide epitopes. The results presented herein show that the in vivo-generated antibodies bind to the respective epitope/antigenic determinant on the alpha 1-subunit of NKA thereby increasing NKA activity. Methods for making, isolating and purifying NKA activity-increasing antibodies and the above-identified peptide antigenic determinants are described in U.S. Patent Applications 20040057956 and 20030228315, the entire contents of which are hereby incorporated by reference as if fully set forth herein.

NKA activity is known to be low in aging and certain diseases, such as Alzheimer's disease [32-34], aging [35], kidney diseases and hypertension [36-38], obesity [39], insulin resistance and complications [40-45], diabetes [46, 61], lung diseases [47], colitis [48], Rye's syndrome [49], liver diseases [50], urinary tract diseases [52], intestinal diseases [53-54], hemorrhagic shock [55], cataracts [56-57], and other diseases of the nervous system [58-60] or heart associated with low levels of NKA activity. The NKA pump has been well studied for its role in the regulation of ion homeostasis in mammalian cells. Recent studies suggest it might have multiple functions such as a role in the regulation of tight junction structure and function, induction of polarity, regulation of actin dynamics, control of cell movement, and cell signaling. These functions appear to be modulated by NKA activity as well as protein-protein interactions of the alpha and beta subunits. A reduction or impairment of NKA function or reduced subunit expression levels have been implicated in kidney diseases such as cancer, tubulointerstitial fibrosis, and ischemic nephropathy. [50] Until the discovery of the active sites on NKA and of NKA activity-increasing antibodies as described herein, there was no known agent that could be used to prevent or treat such diseases by stimulating NKA activity. Therefore some embodiments of the present invention are directed to methods for preventing or treating diseases associated with decreased NKA activity by administering to a diseased animal one or more NKA activity-increasing antibodies or antibody fragments or a small molecule that binds to an active site on NKA, in an amount that increases NKA activity in the appropriate cells or tissues. In some embodiments the one or more NKA activity-increasing antibodies are administered systemically, for example to increase NKA activity in red blood cells or endothelium, or locally for example to treat cataracts.

In another embodiment, the invention provides a method for increasing NKA activity by administering to an animal a vector carrying a gene that encodes one or more of the five amino acid sequence epitopes on NKA [DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4)], and variants, derivatives or fragments thereof. The vectors can be made using any technique known in the art of recombinant DNA or RNA technology. The in vivo expression of the antigenic determinants or epitopes acts like a vaccine causing the host immune system to generate the respective one or more NKA activity-increasing antibodies. In preferred embodiments, these vectors are under the control of tissue specific promoters so that the vectors can be optimally expressed in the targeted cell or bodily fluid. Such tissue specific promoters come from tissues including pancreas, endothelium, epithelium, kidney, liver, bladder, intestine, colon, brain, neurons, the gastrointestinal tract, heart, lung, muscle, and nervous system. These vectors can also be used to generate sera comprising the NKA activity-increasing antibodies using standard methods such as immunizing mammals.

Some embodiments of the present invention are directed to the new antibody SSA401; to pharmaceutical compositions that contain the antibody or a fragment thereof, and to its therapeutic use to treat diseases associated with low NKA activity, including heart diseases and contractile disorders. This antibody, like the others, can be monoclonal or polyclonal and humanized. Another embodiment is directed to the peptide HLLGIRETWDDRWIN (SEQ ID: 4), and to its use as a diagnostic agent for treating or preventing heart disease or other contractile disorders, by detecting, in standard assays, such as ELISAs, RIAs and the like, peptides which are indicative of contractile disorders. In another preferred embodiment, the invention provides for pharmaceutical compositions comprising the HLLGIRETWDDRWIN (SEQ ID: 4) peptide (or fragment, derivative or variant) for treating or preventing heart diseases and contractile diseases.

The Alpha 1-Subunit is a Highly Conserved Antigenic Site in NKA Isoforms

The functional NKA comprises a 113-kDa catalytic alpha ($\alpha$) subunit together with a noncatalytic 35-kDa beta ($\beta$) subunit and appears to exist as an heterodimer. NKA couples the hydrolysis of one molecule of ATP to the outward translocation of three sodium ions and inward translocation of two potassium ions against their steep electrochemical gradients. Thus NKA maintains the normally high-potassium and low-sodium concentrations in the cytoplasm of animal cells. Kinetic experiments have indicated that the catalytic alpha subunit can exist in at least four conformations as it passes through each turnover. The four conformations are $E_1$, $E_{1-P}$, $E_{2-P}$, and $E_2$. It is thought that $E_1$ is the inward-facing form of the enzyme, which normally releases $K^+$ as a product and receives $Na^+$ as a substrate. The $E_1$ conformation has high affinity for ATP and participates in sodium-dependent phosphorylation to form $E_{1-P}$. The $E_{1-P}$ conformation is the one in which the protein has surrounded the three $Na^+$ ions on their way to the outside. The $E_{2-P}$ conformation is the outward-facing form and releases the three $Na^+$ ions as products and receives the two $K^+$ ions as substrates. Upon dephosphorylation, the $E_2$ conformation is formed. This conformation surrounds the two $K^+$ ions and has low affinity for ATP. It is during the transitions among these four forms that the cations traverse the plasma membrane. All isoforms of the alpha subunit of NKA share the same enzymatic function. Therefore any antibody or small molecule that binds to any of the five activation sites described herein or to a fragment, derivative or variant of the activation site of any of the isoforms of NKA increases the enzymatic activity.

NKA regulates both excitability and contractility of the heart. Previous studies by our laboratory identified the SSA 412, 78, 95 and 97 antibodies that recognize specific sites in the extracellular domain of the alpha subunit (also referred to as "$\alpha$1") rat NKA. [12, 31-32], the entire contents of which is incorporated by reference as if fully set forth herein. The SSA412 antibody (also referred to as the KX-1 antibody) and the SS78 antibody (also referred to as the Jianye-2 antibody) are described in detail in the US Patent Application No. 20040057956; the SSA 95 and SSA 97 antibodies are described in US Patent Application No. 20030228315, the entire contents of which is incorporated by reference as if fully set forth herein. These four antibodies were shown to have therapeutic use for treating or preventing heart diseases and contractile disorders by producing a positive ionotropic effect and increasing muscle contraction. A new antibody SSA401 has now been discovered that posses these ionotropic properties in addition to being able to increase NKA activity.

Most of the detailed experiments on NKA activity were done using the site-specific antibody SSA412 made against the D-R region [18, 19], which resides within the extracellular H7-H8 domain of rat $\alpha$1 NKA (FIG. 1A). Comparison of amino acid sequences shows that the D-R region is highly conserved: it is identical for $\alpha$1 NKA in different species [3, 18-22], 87% identity between $\alpha$1 and $\alpha$2 [18, 19, 23], and 93% for $\alpha$3 [18, 19, 24] isoform (FIG. 1A). Therefore antibodies that work in rodents, will work similarly in higher mammals. Using immunoprecipitation and Western blotting, we examined the interaction between SSA412 and its antigenic site on NKA. SDS gel electrophoresis reveals that SSA412 specifically binds to and precipitates NKA (FIG. 1B-B) from rat heart cell lysates (FIG. 1B-C). This is confirmed by highly purified dog NKA (FIG. 1B-A) and a control antibody SSA78 (FIG. 1B-D), which targets the H1-H2 domain of the enzyme [12]. Western blots show that SSA412 and SSA78 recognize the $\alpha$-subunits of NKA (FIG. 1B-E and FIG. 1B-D). Since only high population $\alpha$1 and low $\alpha$2 are expressed in rat heart, the results of Area-Density Calculation (LabWorks analysis software, Ultraviolet Products Bioimaging Inc., Upland, Calif., USA) show that SSA412 immunoprecipitates 95% $\alpha$1 (FIG. 1B-E) and 5% $\alpha$2 (FIG. 1B-H) from isolated rat cardiomyocytes. SSA412 co-precipitates $\alpha$3 NKA from rat brain homogenates (FIG. 1B-J). These data suggest that SSA412 interacts with its antigenic site which is highly conserved in NKA isoforms. SERCA2 antibody recognizes $Ca^{2+}$-ATPase from SR vesicles (FIG. 1B-K), but SSA412 does not cross-react with SR $Ca^{2+}$-ATPase (FIG. 1B-L).

NKA is Activated by Antibodies that Bind to the Alpha 1-Subunit

NKA is a ubiquitous and critical enzyme for electrolyte balance that was discovered a half century ago. [1] Although NKA activity is depressed in many diseases, no one has found a means for activating this enzyme until now. Previous studies in cardiac myocytes showed that the binding of antibodies SSA412, SSA95, SSA97, and SSA78 to extracellular sites in the alpha-subunit of NKA produced various physiologic effects, i.e. the increase in calcium transients and myocyte contraction. Cardiac glycosides that also have positive ionotropic effects in cardiac myocytes were presumed to work by inhibiting NKA. Here we show that the native catalytic power of NKA is markedly elevated when antibody-enzyme interaction occurs at various extracellular regions in the $\alpha$-subunit of the enzyme. The results of the experiments described herein show that the binding of antibodies SSA412, SSA95, SSA97, SSA78 and SSA 401 to extracellular sites in the alpha 1-subunit of NKA activates the enzyme. These antibodies also recognize the similar sites on isoforms of NKA. Because the extracellular peptide regions of the alpha 1-subunit of NKA to which the antibodies bind are highly conserved among species and among tissues within a species, these antibodies have wide therapeutic application to treat any disease or metabolic imbalance in an animal that is associated with lower than normal levels of NKA activity. Energy deficiency and dysfunction of the NKA are common consequences of many diseases.

Example 1 below describes how the activation of NKA induced by various antibodies was determined. Example 2 describes Immunoprecipitation, blotting, and immunofluorescent staining of the antibodies. Example 3 describes the methods for measuring physiologic indices of intracellular $Ca^{2+}$ transients and cell contraction in cardiac myocytes. Example 4 describes the Isolation of sarcolemmal vesicles and the purification of NKA. Example 5 describes methods of measuring NKA activity, and Example 6 describes methods of measuring NKA phosphorylation.

Figure 2A:
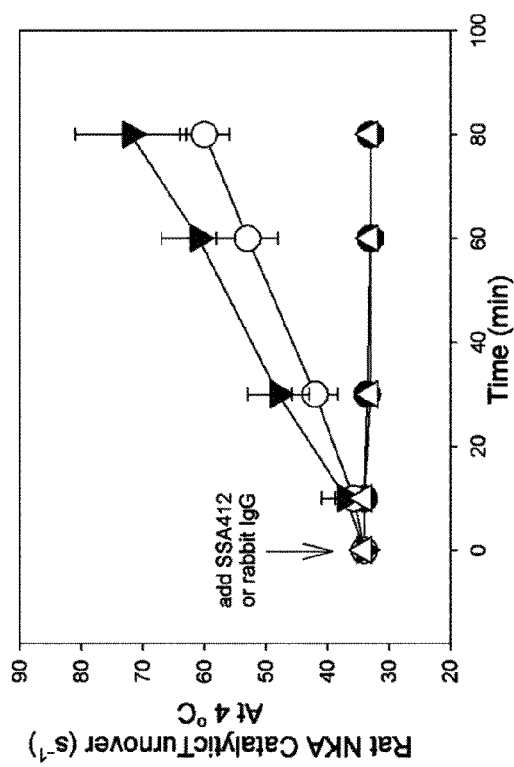
FIG. 2A and FIG. 2B show the time course of activation of purified rat (FIG. 2A: 0.125 mg/ml, ouabain-resistant) or dog (FIG. 2B: 0.125 mg/ml, ouabain-sensitive) NKA incubated with SSA412 (0.5 and 1.0 μM) or with 1.0 μM normal rabbit total IgG at 4° C., or at room temperature FIG. 2C and FIG. 2D. NKA activity was monitored at 0, 10, 30, 60, and 80 min time point for experimental conditions in A and B, and 0, 10, 30, 60, 90, 120 min for conditions in FIG. 2C and FIG. 2D.
Figure 2B:
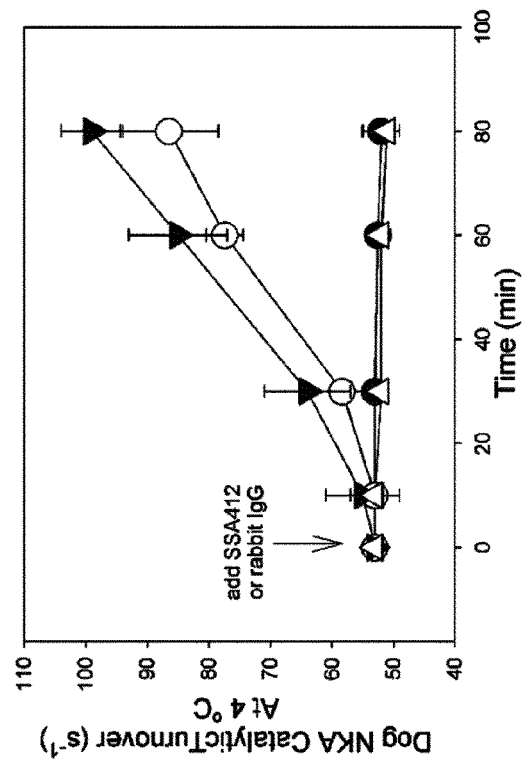
Figures 2C, 2D:
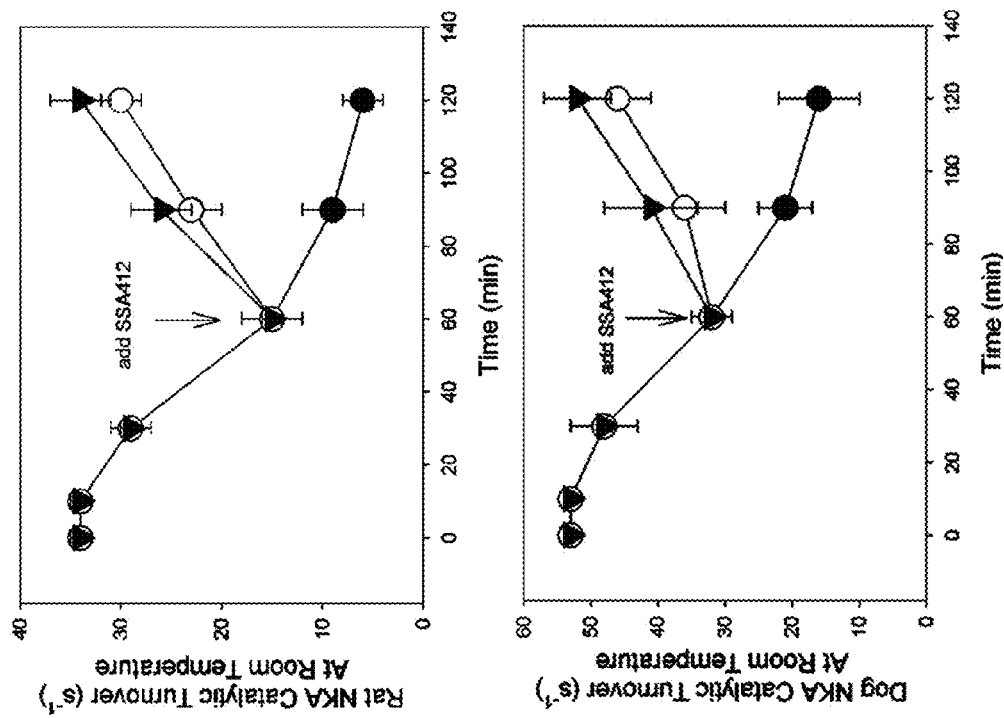

A first series of experiments were conducted testing whether antibody SSA412, binding to the D-R region of the alpha 1-subunit, affects NKA activity. NKA activity was determined based on Jack Kyte's method as previously described [17, which is hereby incorporated by reference as if set forth fully herein]. The results presented below show that NKA activity levels can be increased by SSA412 antibody binding. FIG. 2A and FIG. 2B show the time course of activation of purified rat (FIG. 2A: 0.125 mg/ml, ouabain-resistant) or dog (FIG. 2B: 0.125 mg/ml, ouabain-sensitive) NKA incubated with SSA412 (0.5 and 1.0 µM) or with 1.0 µM normal rabbit total IgG at 4° C. or at room temperature (FIG. 2C and FIG. 2D). The control is indicated by closed circles, 0.5 mM SSA412 by open circles, 1.0 mM SSA412 by closed triangles and 1.0 mM rabbit IgG by open triangles.

Different concentrations of SSA412 (0.5 or 1.0 µM) were incubated with purified ouabain resistant- (rat) and sensitive- (dog) NKA prior to ATPase assay [17]. FIG. 2A and FIG. 2B show that SSA412 markedly activated both rat and dog NKA function. The catalytic turnover of rat NKA was 34, 36, 42, 53, and 60 $s^{-1}$ following 0, 10, 30, 60, and 80 min incubation with 0.5 µM SSA412 at 4° C., and 34, 37, 48, 61, 72 $s^{-1}$ with 1.0 µM SSA412 (FIG. 2A). Under the same experimental conditions as for rat NKA, the turnover of ouabain-sensitive dog NKA also increased. NKA in dog was 53, 54, 58, 77, 86 $s^{-1}$ with 0.5 µM SSA412, and 53, 55, 64, 85, 99 $s^{-1}$ with 1.0 µM SSA412 (FIG. 2B). By contrast, no significant changes in control samples (without SSA412) and in the presence of 1.0 µM total rabbit IgG for both rat and dog enzymes (FIG. 2A and FIG. 2B) were found, indicating the specificity of SSA412-induced activation of NKA. These results suggest that NKA catalytic activity can be significantly enhanced beyond normal levels by binding with SSA412 antibody, and that the D-R region is an effective site of NKA activity.

This novel NKA activation was verified at room temperature (RT) using the same SSA412 concentrations, except that SSA412 was added to the samples after 60 min. In the absence of the enzyme substrate MgATP, the activity of purified NKA is gradually denatured at RT as a function of time as shown in FIG. 2C and FIG. 2D (black circles). When partially inactivated NKA was exposed to SSA412, it remarkably protected both rat and dog enzyme functions by enhancing NKA catalytic turnover against further denaturing: rat NKA turnover was 16 $s^{-1}$ (FIG. 2C, black circles) following 60 min at RT before exposure to SSA412, and increased to 23 and 29 $s^{-1}$ after incubation with 0.5 µM SSA412 for 30 and 60 min, respectively (FIG. 2C, open circles). Under the same partially inactivation conditions, rat NKA turnover was further accelerated to 27 and 34 $s^{-1}$ in the presence of 1.0 µM SSA412 (FIG. 2C, black triangles). A similar phenomenon was also observed for dog NKA: enzyme catalytic turnover was 32 $s^{-1}$ at RT for 60 min (partial inhibition state at RT), and increased to 36 and 46 $s^{-1}$ after exposure to 0.5 µM SSA412 for 30 and 60 min, and 41 and 52 $s^{-1}$ with 1.0 µM SSA412 under the same experimental conditions.

Figures 3A, 3B:
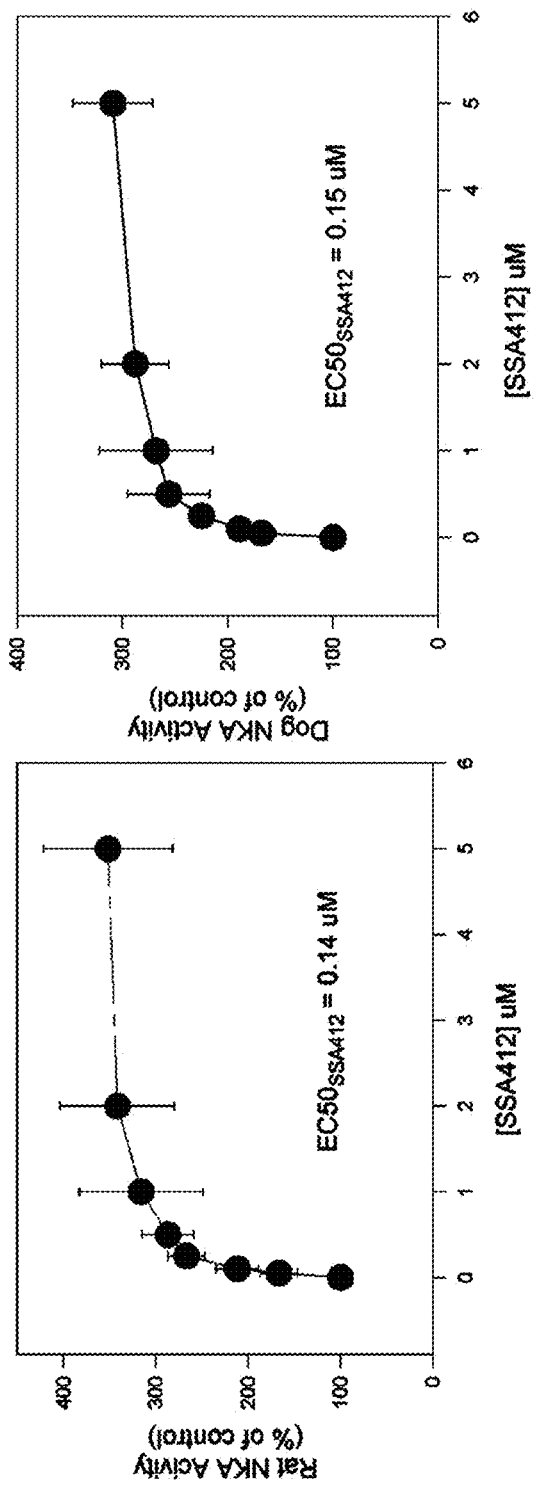
FIG. 3A and FIG. 3B show that NKA activity is a function of the concentration of SSA412: Purified dog (FIG. 3B, 1.25 μg/ml) and rat (FIG. 3A, 6.25 μg/ml) NKA.

Activation of NKA was further examined by the determination of the effective concentration of SSA412. Purified dog (1.25 µg/ml) and rat (6.25 µg/ml) NKA were incubated at the different concentrations of SSA412 for 60 min prior to the standard ATPase assay. Purified dog (FIG. 3A, 1.25 µg/ml) and rat (FIG. 3B, 6.25 µg/ml) NKA was used. Experimental results show that the rate of activation of NKA is a function of the concentration of SSA412. The maximum turnover of the enzyme is over 2 times faster than that of the controls for both ouabain-resistant (FIG. 3A) and ouabain-sensitive NKA (FIG. 3B). The half effective concentration ($EC_{50}$) of SSA412 is 0.14 µM for rat and 0.15 µM for dog NKA. These data demonstrate that the D-R region is an important effective site of NKA and that SSA412 is a novel effector to stimulate NKA activity, in which interaction with the enzyme elevates the NKA-catalyzed reaction.

Characteristics of NKA Activation

Figure 3F:
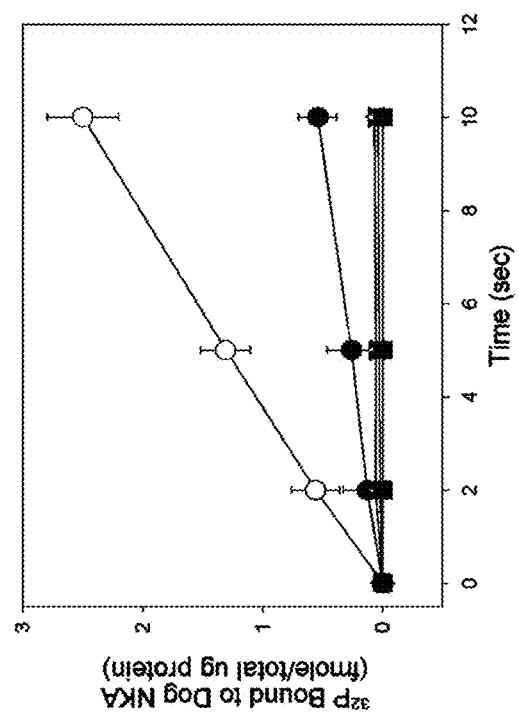
FIG. 3E and FIG. 3F show the effect of SSA412 on phosphorylation of NKA: Purified rat (FIG. 3E) or dog (FIG. 3F) NKA (17 nM) was phosphorylated in the presence of 100 mM Sodium or 20 mM K, 10 μM MgATP, and 1 nM [γ-$^{32}$P]ATP with or without SSA412. For both FIG. 3E and FIG. 3F black circles indicate control: enzyme with sodium; open circles are with sodium plus 1 μM SSA412; closed triangles are with potassium plus 1 μM SSA412, open triangles are with sodium plus 1 μM rabbit IgG, and closed triangles are without enzyme plus sodium plus 1 μM SSA412.
Figure 3E:
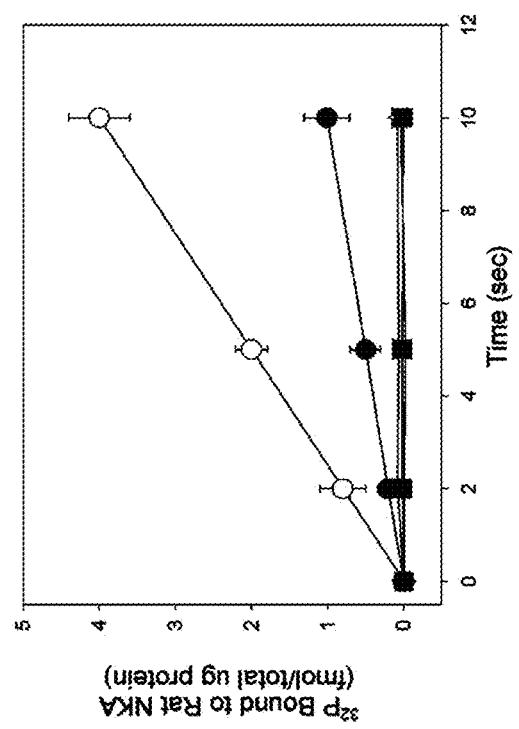

Hydrolysis of MgATP is one of the fundamental components of the catalytic function of NKA. The Michaelis constant ($K_m$) indicates the mode of regulating the activity of an enzyme. The effect of SSA412 on the numerical value of $K_m$ of MgATP in the activation of NKA was next determined. In the presence of 0.5 µM of SSA412 with different MgATP concentrations, the $K_m$ values were lowered 16 and 15% for rat and dog NKA while maximum enzyme activity (or enzyme turnover) increased in both cases (FIG. 3C and FIG. 3D). Moreover, binding of SSA412 to NKA promotes the net $^{32}$P-phosphorylation labeling (FIG. 3E and FIG. 3F), confirming that SSA412-activated NKA is based on the enhanced rate of MgATP hydrolysis. No changes occurred in the $^{32}$P-phosphorylation labeling in the absence of SSA412 or presence of total rabbit IgG.

Figures 3G, 3H:
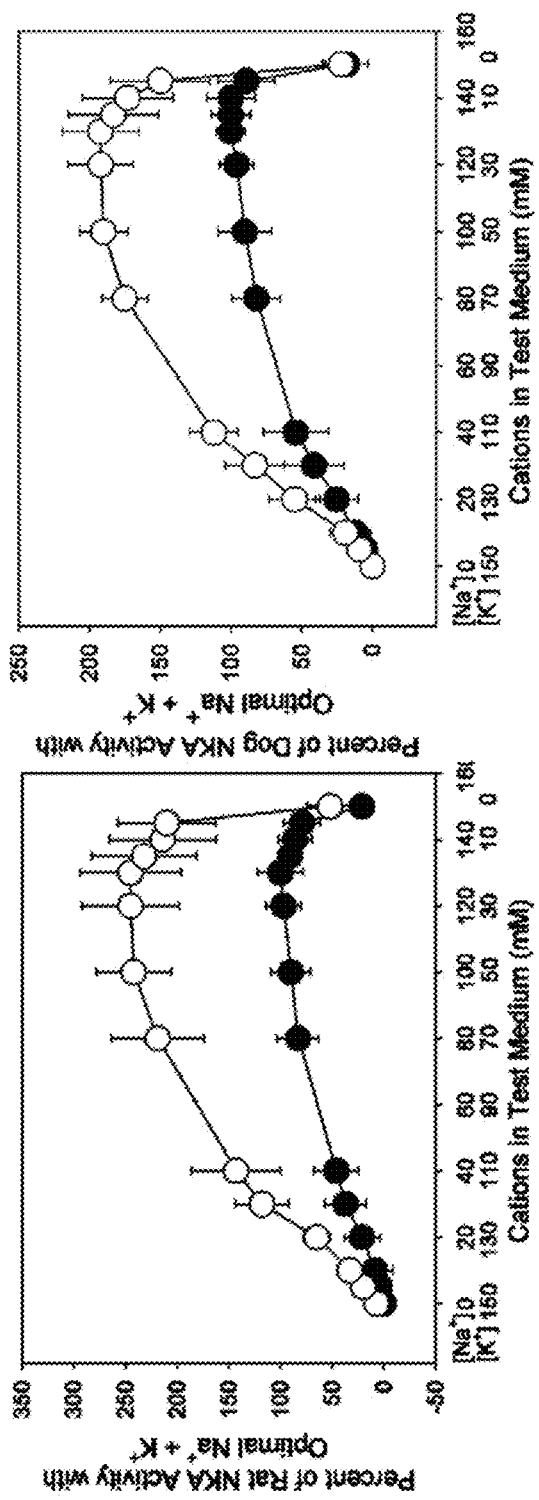
FIG. 3G and FIG. 3H show that binding of SSA412 causes no changes in the apparent $Na^+$:$K^+$ affinity ratio for the enzyme function, while accelerating NKA turnover rate. Each data point represents a mean of four to five experiments. For both FIG. 3G and FIG. 3H, closed circles are controls and open circles are plus 0.5 μM SSA412.

NKA-catalyzed hydrolysis of MgATP is a function of $Na^+$ plus $K^+$ concentrations [25]. It was next determined whether the binding of SSA412 to the D-R region of NKA would affect local $Na^+$/$K^+$ binding concentrations and ion active transport. No significant changes in the optimal binding concentrations of $Na^+$ and $K^+$ were detected while NKA activity and $Na^+$/$K^+$ ion transport were significantly increased (FIG. 3G and FIG. 3H, open circles). To confirm the SSA412-enhanced $Na^+$/$K^+$ ion transport, we investigated the effect of SSA412 on the initial rate of $Na^+$ and $K^+$ transport separately. When the cytoplasmic site of the enzyme is saturated with 100 mM $Na^+$ and 3 mM MgATP, the initial rate of $K^+$ transport increased two-fold with 5 mM $K^+$ in the presence of 1 µM SSA412 (Table 1). The same is true for $Na^+$ transport, SSA412 also doubled the initial rate of $Na^+$ transport while the extracellular site is saturated with 20 mM $K^+$ and 3 mM MgATP in the presence of 20 mM $Na^+$ (Table 1). Condition 1: [$Na^+$]=100 mM, [$K^+$]=5 mM. Condition 2: [$Na^+$]=20 M, [$K^+$]= 20 mM. In both conditions: [MgATP]=3 mM, SA412]= 1 µM.

TABLE 1

SSA412 ENHANCES THE APPARENT INITIAL RATE OF SODIUM AND POTASSIUM TRANSPORT UNDER DIFFERENT EXPERIMENTAL CONDITIONS (N = 5)

| Samples | Condition 1<br>$K^+$-regulated initial rate<br>(µmol Pi $mg^{-1}$ $min^{-1}$) | Condition 2<br>$Na^+$-regulated initial rate<br>(µmol Pi $mg^{-1}$ $min^{-1}$) |
|---|---|---|
| Rat NKA Control | 1.82 ± 0.2 | 1.64 ± 0.1 |
| Rat NKA + SSA412 | 4.03 ± 0.5 | 3.64 ± 0.4 |
| Dog NKA Control | 21.8 ± 1.6 | 14.5 ± 2.1 |
| Dog NKA + SSA412 | 45.7 ± 4.7 | 30.8 ± 3.3 |

Mechanisms of Activation of NKA-Mediated Biological Processes

Figure 4A:
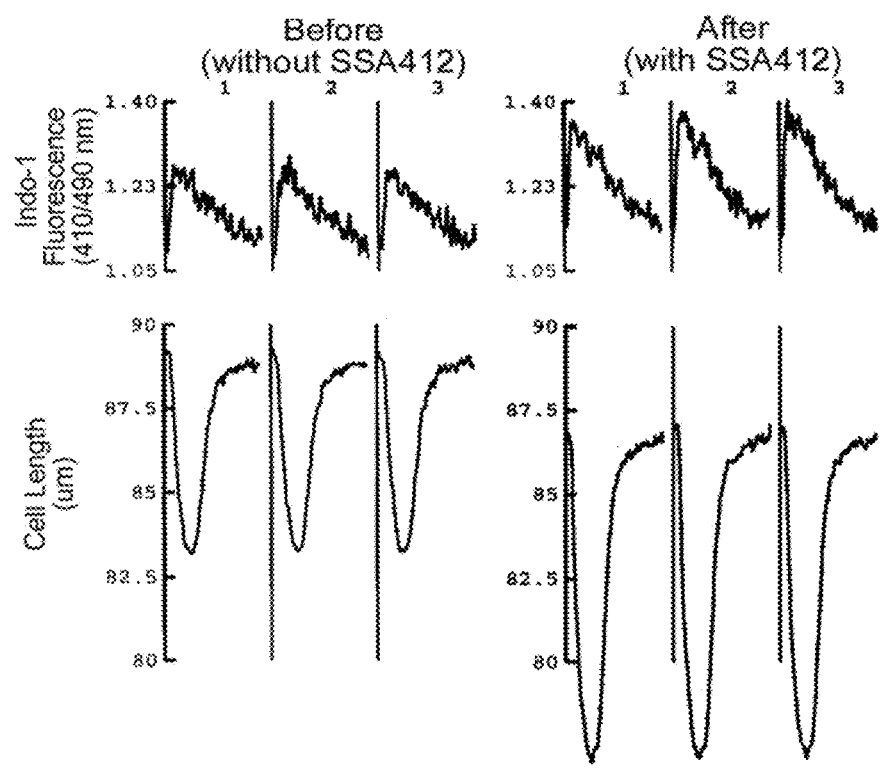
FIG. 4A and FIG. 4B show representative illustrations of the effect of SSA412 on $Ca^{2+}$ transient amplitude (top trace) and contraction (bottom trace) of Indo-1/AM-loaded rat heart cells (FIG. 4A) before and after administration of SSA412

It was known from previous work by our laboratory that SSA412, SSA78, SSA95 and SSA97 elicit a positive ionotrophic response in cardiac myocytes, but the mechanism of action was not known. Here we show that when isolated rat myocyte is loaded with the calcium indicator Indo-1/AM, binding of SSA412 (0.25 µM) to NKA increased both myocyte intracellular $Ca^{2+}$ transient amplitude (1.24-fold, n=20) (FIG. 4A upper trace) and contraction (1.67-fold, n=20) (FIG. 4A lower trace). The increase in calcium and contraction was blocked with a peptide blocker DVEDSYGQQWTYEQR (SEQ ID: 5). These results reveal that activation of NKA generates a positive inotropic effect and suggests that amino acids residing in the D-R region may be vital residues to NKA activity, which plays an important role in cardiac regulation.

Figure 4B:
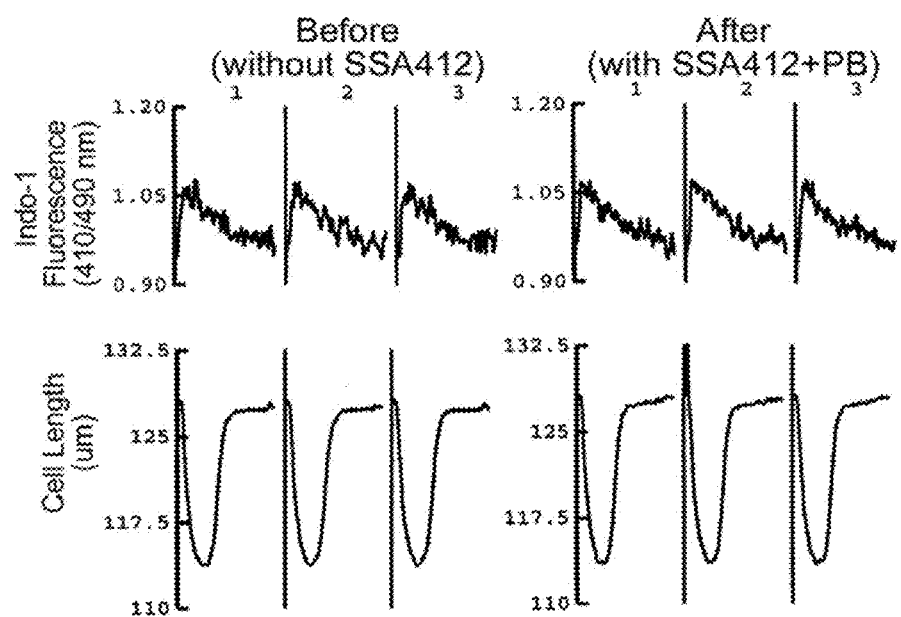
Figure 4C:
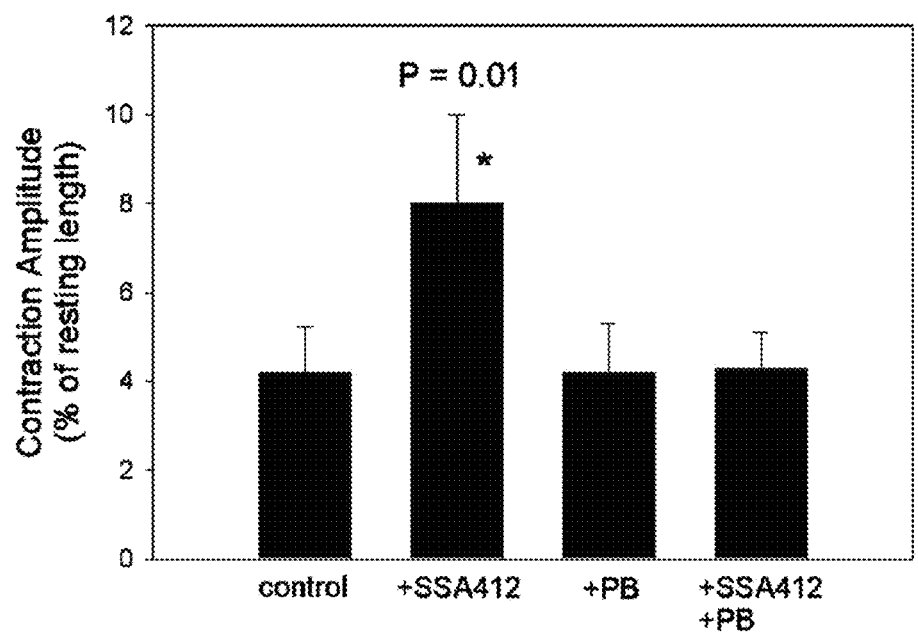
FIG. 4C shows the average changes of cell contraction for FIG. 4A and FIG. 4B.
Figure 4D:
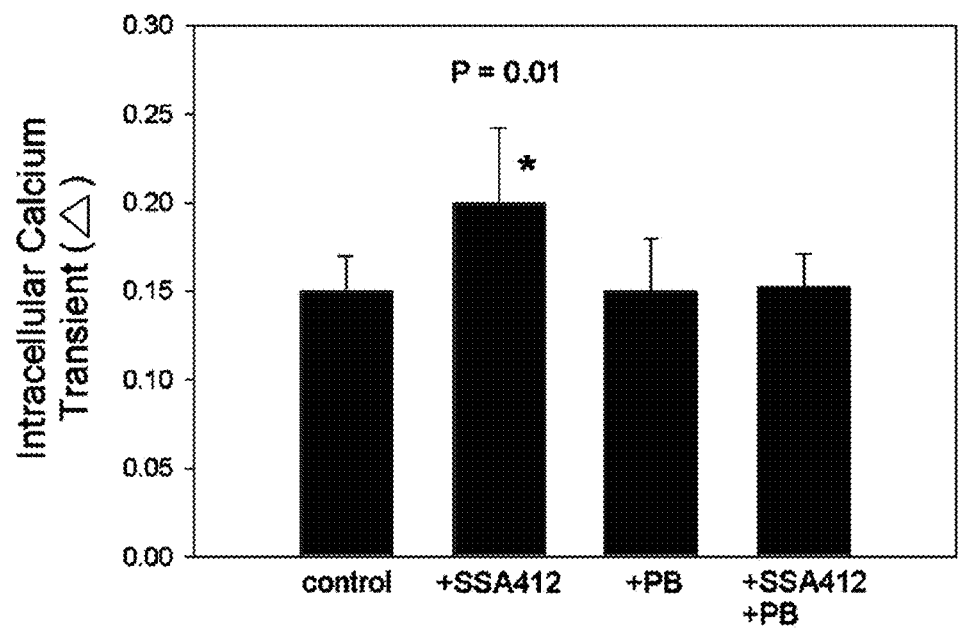
FIG. 4D shows the average changes of $Ca^{2+}$ transient for FIG. 4A and FIG. 4B. Data are presented as % of control based on 20 independent measurements. PB=peptide blocker.

FIG. 4C shows the average changes of cell contraction for FIG. 4A and FIG. 4B. FIG. 4D shows the average changes of the $Ca^{2+}$ transient for FIG. 4A and FIG. 4B. Data are presented as % of control based on 20 independent measurements. PB=peptide blocker.

Figure 8A:
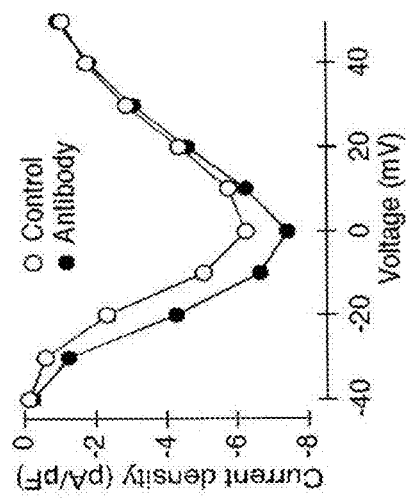
FIG. 8A: time course of peak $I_{Ca}$ before and after administration of 1 µM SSA412, where the currents were elicited every 10 sec.
Figure 8B:
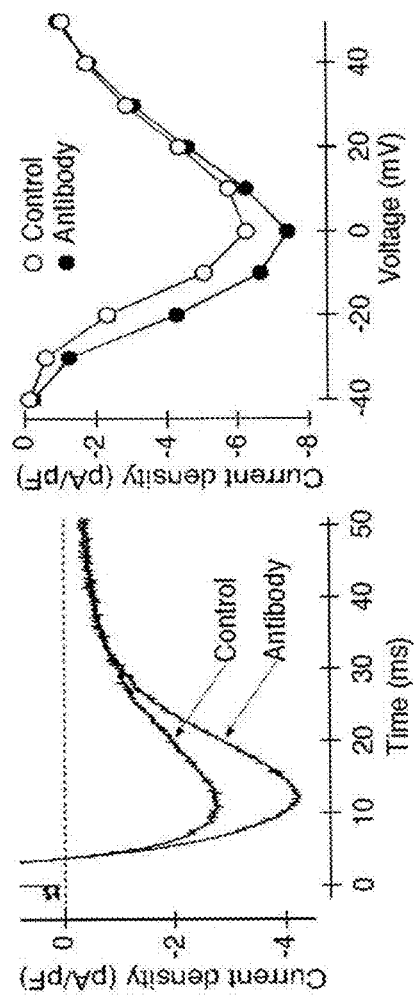
FIG. 8B: representative current traces recorded at −20 mV. C: current-voltage relations I-V curves) before and after antibody application. The results indicate that activation of NKA increases LTCC function. Each of the data represents one of ten similar results.
Figure 8C:
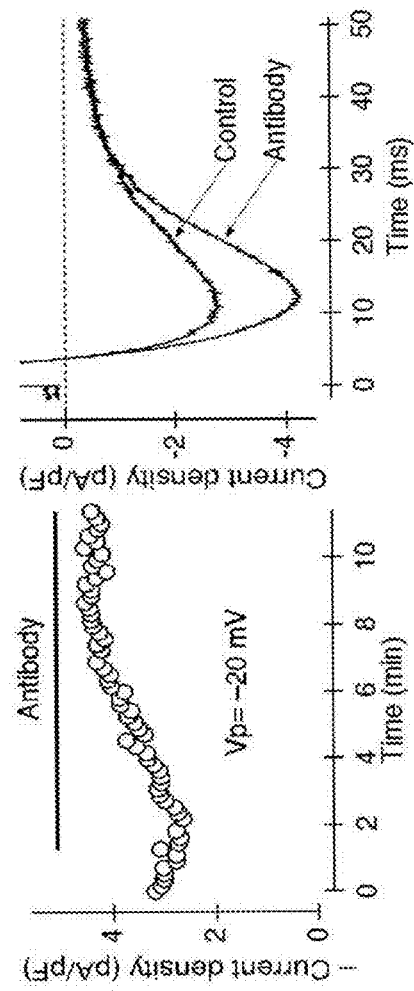
FIG. 8 shows the effect of SSA412 on whole-cell L-type calcium channel (LTCC) current of isolated rat myocytes.

To understand the mechanisms underlying the biological activity of these inotropic antibodies and activation of the NKA-induced increase of calcium ion transients and muscle contraction, we tested whether activation of NKA affects cardiac L-type $Ca^{2+}$-channel (LTCC) function. It was discovered that cardiac LTCC activity is increased following exposure to antibody SSA412 in isolated adult rat myocytes (FIGS. 8A, 8B and 8C). No significant changes occurred in the absence of SSA412 (before adding antibody). These data directly link LTCC activity to the activation of NKA-regulated increase of $[Ca^{2+}]_i$ and cardiac contraction.

We next tested the functional relationship between activation of NKA-induced enhancement of LTCC current and sarcoplasmic reticulum (SR) calcium release in rat neonatal myocytes. FIG. 9 shows that the binding of SSA412 to NKA activates LTCC activity, which simultaneously triggers SR calcium release in rat neonatal ventricular myocytes grown on cover slips and voltage-clamped ('whole-cell' patch-clamp). The data suggest that (a) SR calcium is involved in the mechanistic pathways of activation of NKA-mediated cardiac contraction, and (b) LTCC-regulated $Ca^{2+}$-induced $Ca^{2+}$-release (CICR) may account for how activation of NKA triggers the positive inotropic effect.

Figure 10:
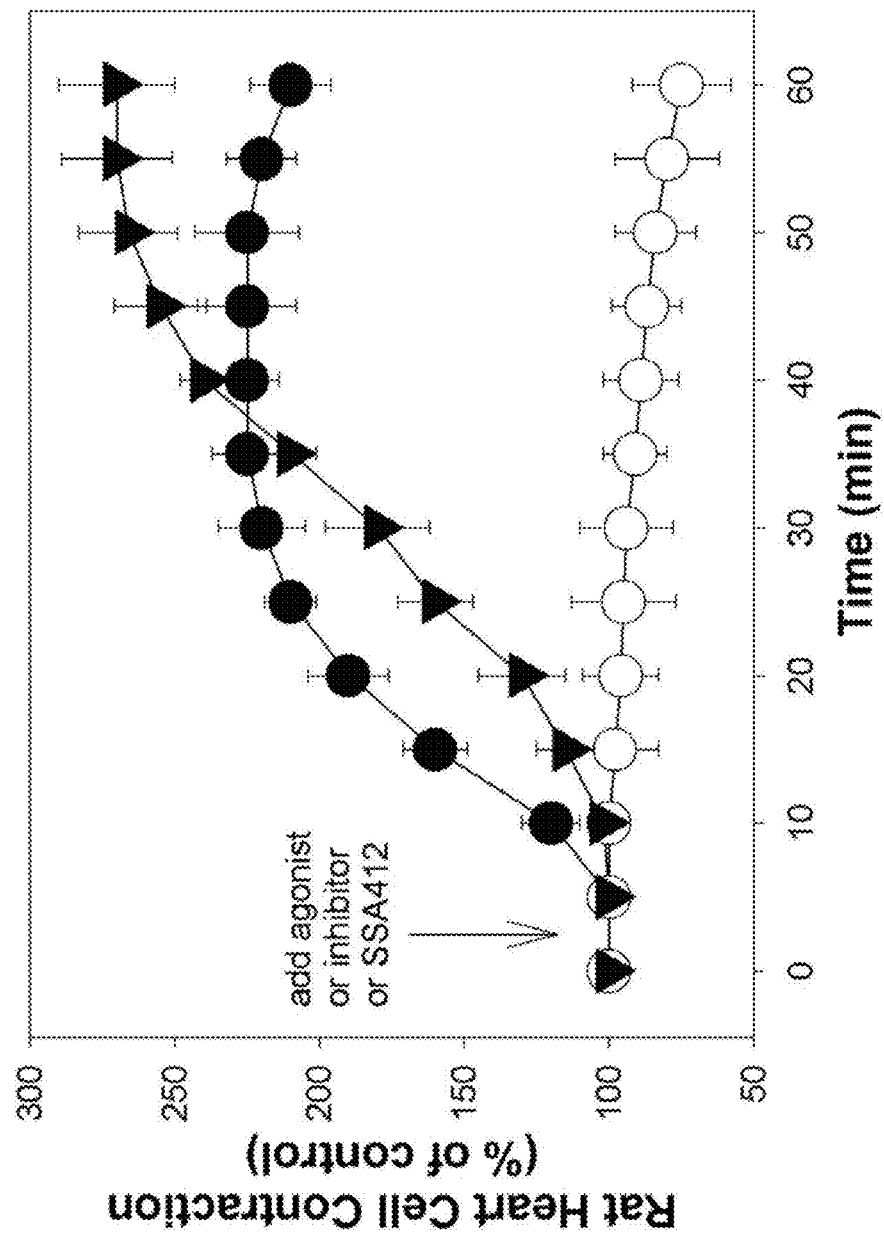
FIG. 10 shows the time course of the effect of α- and β-adrenergic receptor inhibitors on activation of the NKA-induced positive inotropic effect in isolated rat myocytes. Cell contractions were measured in the presence or absence of SSA412 (0.5 µM) with or without inhibitors. Black circles: with 1 µM isoproterenol. Open circles: with 1 µM isoproterenol+both prazosin and propennol (7 µM each). Black triangles: with SSA412 in the presence of both prazosin and propennol (7 µM each). Data are presented as percent of control (n=8 cells for each group). Inhibitors did not affect the biological effect of SSA412 while completely abolishing the activity of agonist isoproterenol.

Adrenergic receptors play important role in regulating cardiac contraction. To see whether the α- and β-adrenergic receptors are involved in the activation of NKA-regulated LTCC activity, we looked at the time course of the effect of α- and β-adrenergic receptor inhibitors on activation of the NKA-induced positive inotropic effect. FIG. 10 shows that neither the α-adrenergic receptor inhibitor prazosin nor the β-adrenergic receptor inhibitor propenol (7 μM each) affected activation of the NKA-induced positive inotropy, while both inhibitors eliminated action of the agonist isoproterenol. The data demonstrate that activation of NKA-induced biological action is independent of α- and β-adrenergic receptor-mediated pathways.

Figure 11:
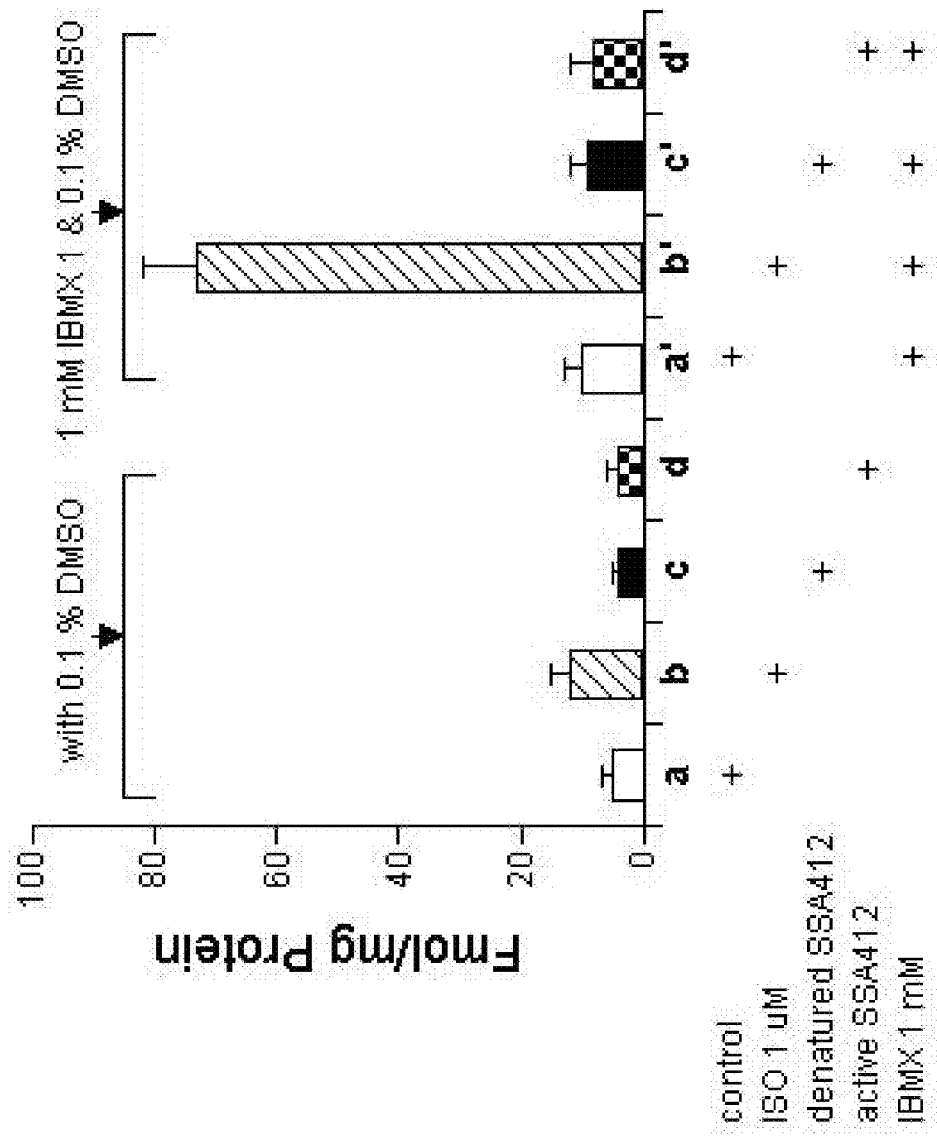
FIG. 11 shows that activation of NKA has no effect on cyclic AMP (cAMP) formation in rat cardiac myocytes. Isolated rat cardiac myocytes were treated with phosphodiesterase inhibitor, 3-isobutyl-1-methylxanthine (IBMX, 1 mM) or DMSO side by side for 30 min at room temperature prior to being incubated with either active SSA412 antibody or boiled SSA412 (4 µM each) for 30 min, or with b-AR agonist, isoproterenol (1 mM) for 5 min as a positive control. Formation of cAMP was assayed using $^3$H-cAMP. Protein concentration was measured using bovine serum albumin as standard. Each of the data represents the mean of three independent experiments.

Cyclic adenosine monophosphate (cAMP) is a very important molecule that controls many biological activities. We further investigated whether cAMP-dependent pathways are involved in the activation of NKA-regulated biological processes. FIG. 11 indicates that activation of NKA has no effect on cAMP formation in isolated rat cardiac myocytes, indicating that activation of NKA-regulated LTCC activity is independent of cAMP signaling pathways.

SSA412 Binding Site is not a Digitalis-Binding Site

Figure 6:
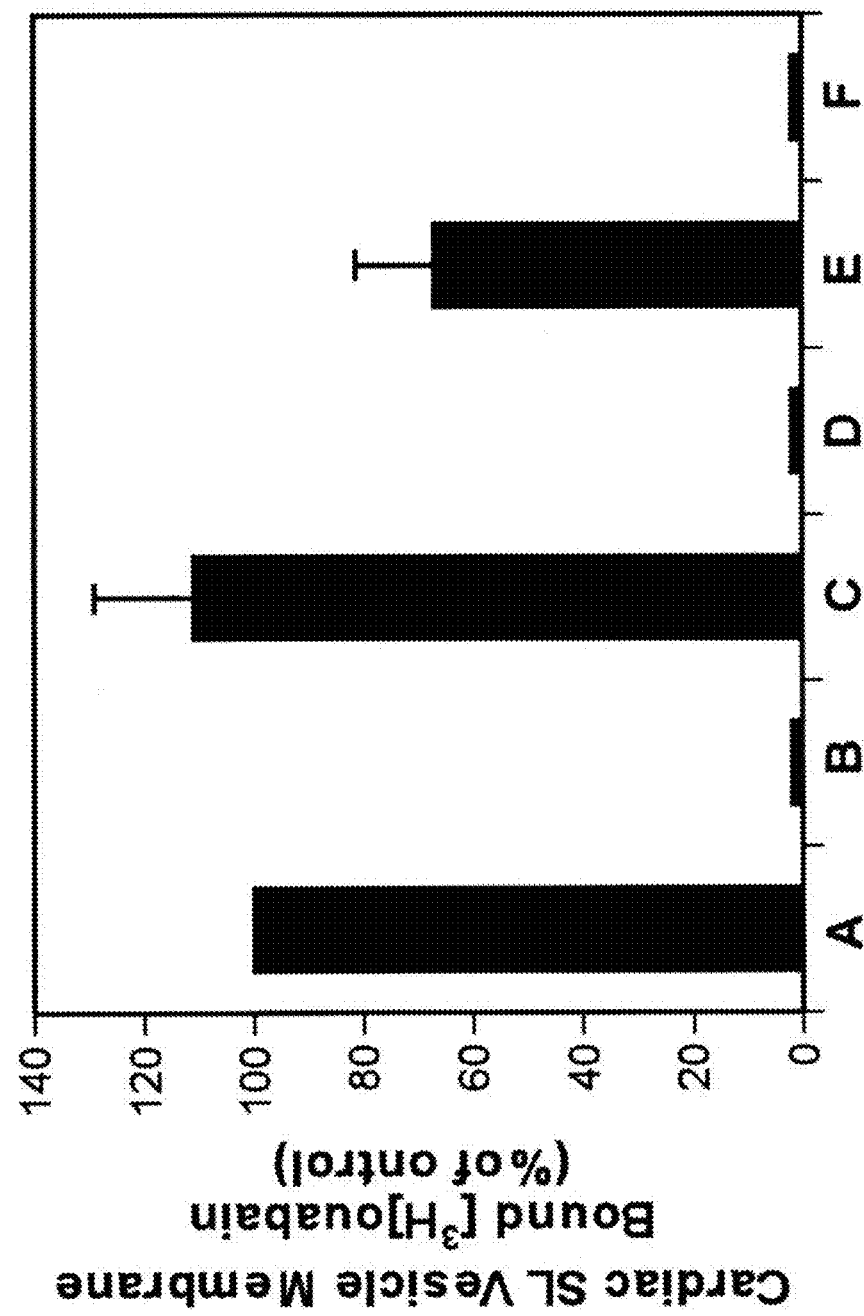
FIG. 6 shows [$^3$H]ouabain binding to rat cardiac sarcolemma (SL) membrane vesicles.

NKA is a target receptor for digitalis and related cardiac glycosides [26-29]. These drugs induce a positive inotropic effect by inhibiting NKA activity [30]. To determine whether the newly discovered effective site is one of the digitalis interacting-sites in NKA, immunofluorescence microscopy was performed on rat heart cells. FIG. 5A shows that SSA412 specifically binds to the D-R region of NKA on the surface of the cell membrane (FIG. 5A and FIG. 5B). Ouabain, at 5, 10, and 20 mM, does not compete with SSA412 binding to the D-R region of NKA (FIG. 5E-H). To verify this observation, a [$^3$H]ouabain labeling experiment was performed. Isolated cardiac sarcolammal membranes right-side-out vesicles were incubated with [$^3$H]ouabain in the presence or absence of SSA412. The results show that SSA412 (1 μM) did not decrease or prevent [$^3$H]ouabain binding to the enzyme. By contrast, the SSA78 (1 μM) made against the H1-H2 domain of the enzyme, reduced the [$^3$H]ouabain labeling by 33% (FIG. 6). These data clearly demonstrate that the D-R region in the α-subunit of NKA is not one of the ouabain interacting sites of the enzyme.

The SSA78, SSA95 and SSA97 Also Increase NKA Activity

Figure 7:
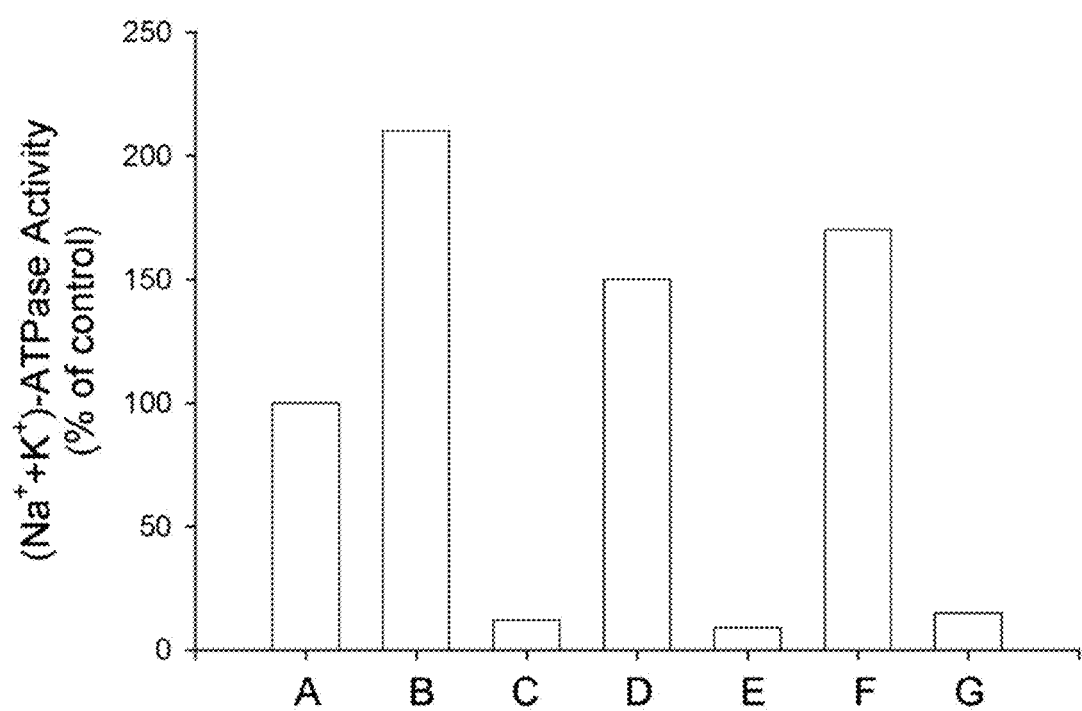
FIG. 7 shows that antibodies SSA95, SSA97, and SSA78 bind to the alpha 1-subunit of NKA and increase ouabain-sensitive dog NKA activity

To see whether there were other activation sites on NKA, the effect of SSA78, SSA95 and SSA97 was tested. FIG. 7 shows that NKA activity in dog, which is ouabain-sensitive, was also increased by activation agents SSA78, SSA95, and SSA97 that bind to the alpha 1-subunit of NKA at amino acid sequences. The antibody-induced increase in NKA by binding to each of these antibodies was blocked with the respective peptide blockers PB78 (RSATEEEPPNDD, SEQ ID: 3), PB95 (KRQPRNPKTDKLVNE, SEQ ID: 1), and PB97 (VPAISLAYEQAESD, SEQ ID: 2).

A New Antibody SSA401 that Binds to the Alpha 1-Subunit is Discovered

Figure 12:
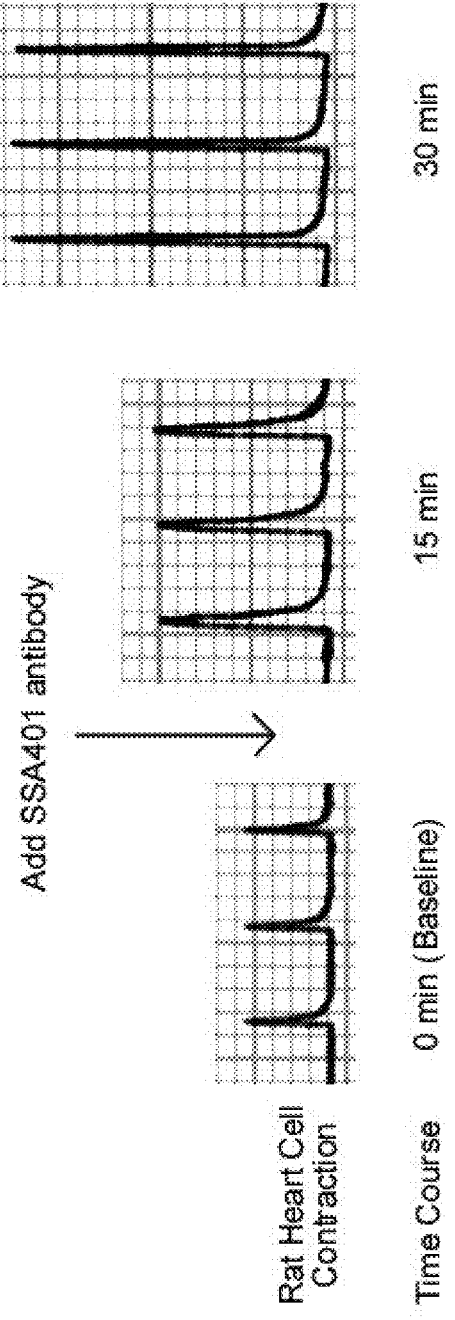
FIG. 12 shows representative results of the time course of rat heart cell contraction with or without SSA401. Time runs from left to right. Control baseline of rat heart cell contractions are shown at zero min. Increased cell contraction as shown at 15 and 30 min following administration of SSA401.

We discovered a new antibody SSA401 (also referred to as the KX-2 antibody) that binds to the alpha 1-subunit of NKA, specifically to the epitope HLLGIRETWDDRWIN (SEQ ID: 4). FIG. 12 shows that the SSA401 antibody strikingly enhanced the velocity of shortening and the force of contraction of isolated rat heart cells. The result indicates that the SSA401 antibody is a new inotropic agent.

Figure 13:
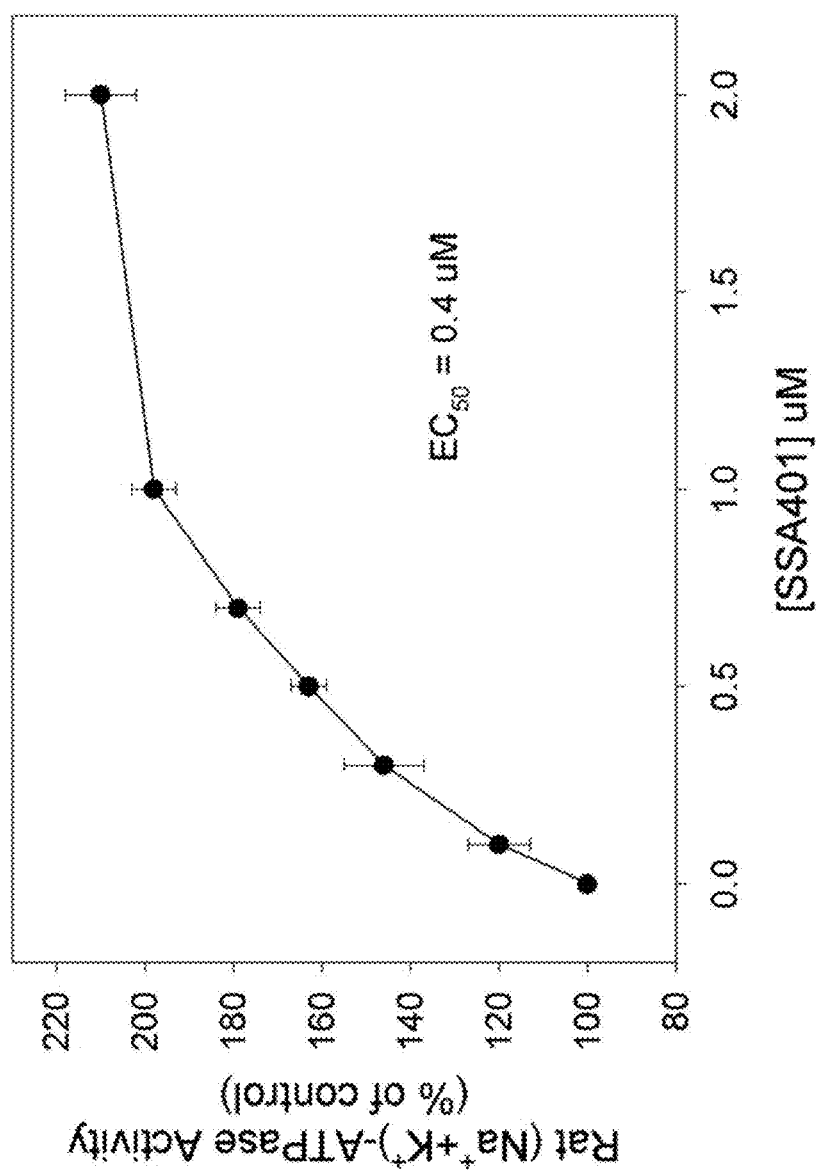
FIG. 13 shows that activation of NKA is a function of the concentration of SSA412. Purified rat NKA (6.25 µg/ml) was incubated with different concentrations of SSA401 (as indicated in the figure) for 60 min at 4° C. prior to enzyme assay.

FIG. 13 shows that the binding of SSA401 to purified NKA activates enzyme function. The catalytic activity of rat NKA was increased by 120±7, 146±9, 163±4, 179±5, 198±5, and 210±8% (compared with the control) in the presence of 0.1, 0.3, 0.5, 0.7, 1.0, and 2.0 μM SSA401, respectively. The half effective concentration ($EC_{50}$) of SSA401 is approximately 0.4 μM. The data indicate that the HLLGIRETWDDRWIN (SEQ ID: 4) region is another activation site of the enzyme and show that the mechanism underlying SSA401 induced positive inotropic effect is based on the activation of NKA. Therefore, an embodiment of the present invention is directed to a new antibody SSA401 in monoclonal, polyclonal and humanized forms. In a preferred embodiment, the invention provides for the therapeutic use of antisera, polyclonal and monoclonal and/or humanized SSA401 antibodies that specifically bind to amino acid the HLLGIRETWDDRWIN (SEQ ID: 4) sequence of the NKA enzyme, for treating patients suffering from or susceptible to heart disease and/or muscle contractile disorders, and for treating or preventing any disease associated with low NKA activity. Certain embodiments are also directed to both exogenous and endogenous SSA401 antibody used to increase cardiac contraction for the treatment of heart failure. This antibody also eliminates the effects of certain precipitating drugs, including negative inotropic agents (e.g., certain calcium channel blockers and antiarrhythmic drugs like disopyramide), cardiotoxins (e.g., amphetamines) and plasma volume expanders (e.g., nonsteroidal antiinflammatory agents and glucocorticoids).

Some embodiments of the present invention are directed to methods for identifying compounds that activate NKA by binding to an activation site. One such method has the steps of a) identifying an assay for quantifying NKA activity, b) using the assay, determining a baseline level of NKA activity in a control sample, c) in a separate peptide binding assay, incubating a compound of interest with a peptide having an amino acid sequence selected from the group comprising DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and fragments, derivatives and variants thereof under conditions that permit the compound to bind to the peptide, d) determining whether the compound binds to the peptide in step c), e) if the compound binds to the peptide, then forming a mixture of the compound and NKA under conditions that permit the compound to bind to the ATPase, f) using the assay of step a) and the same conditions as step b) determining the level of ATPase activity in the mixture, and g) if the level of ATPase activity in the mixture is increased above the baseline level in the control sample determined in step b), then concluding that the compound activates sodium potassium ATPase.

The term "treatment" or grammatical equivalents encompasses the improvement and/or reversal of the symptoms of a disease.

The term "individual" as used herein refers to vertebrates, particularly members of the mammalian species and includes but is not limited to, domestic animals, sports animals, primates and humans; more particularly, the term refers to humans.

As used herein, "contractile disorders" refers to the abnormal contractile response of muscle cells as compared to normal muscle cells. Examples of such disorders are arhythmia, tachyrhithmia, and the like.

Heart disease refers to any heart disease that is responsive to treatment with one or more of the antibodies described herein.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

"Recombinant," as applied to a polynucleotide, means that the polynucleotide is the product of various combinations of cloning, restriction and/or ligation steps, and other procedures that result in a construct that is distinct from a polynucleotide found in nature.

A "gene" refers to a polynucleotide or portion of a polynucleotide comprising a sequence that encodes a protein. For most situations, it is desirable for the gene to also comprise a promoter operably linked to the coding sequence in order to effectively promote transcription. Enhancers, repressors and other regulatory sequences may also be included in order to modulate activity of the gene, as is well known in the art. (See, e.g., the references cited below).

The terms "polypeptide," "peptide," and "protein" are used interchangeably to refer to polymers of amino acids of any length, or derivatives. These terms also include proteins that are post-translationally modified through reactions that include glycosylation, acetylation and phosphorylation.

Peptide "fragment" means any fragment or portion of the peptide.

The terms "variant" and "amino acid sequence variant" are used interchangeably and designate polypeptides in which one or more amino acids are added and/or substituted and/or deleted and/or inserted at the N- or C-terminus or anywhere within the corresponding native sequences used herein, the term "variant" is interpreted to mean a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

The terms "derivatizing" and "derivative" or "derivatized" include processes and all resulting peptides or modified peptides, respectively. Including those in which (1) the peptide or modified peptide has a cyclic portion; for example, cross-linking between cysteinyl residues within the modified peptide; (2) the peptide or modified peptide is cross-linked or has a cross-linking site; for example, the peptide or modified peptide has a cysteinyl residue and thus forms cross-linked dimers in culture or in vivo; (3) one or more peptidyl linkage is replaced by a non-peptidyl linkage; (4) the N-terminus is replaced by —NRR.sup.1, NRC(O)R.sup.1, —NRC(O)OR.sup.1, —NRS(O).sub.2 R.sup.1, —NHC(O)NHR, a succinimide group, or substituted or unsubstituted benzyloxycarbonyl-NH—, wherein R and R.sup.1 and the ring substituents are as defined hereinafter; (5) the C-terminus is replaced by —C(O)R.sup.2 or —NR.sup.3 R.sup.4 wherein R.sup.2, R.sup.3 and R.sup.4 are as defined hereinafter; and (6) peptides or modified peptides in which individual amino acid moieties are modified through treatment with agents capable of reacting with selected side chains or terminal residues.

An "effective amount" is an amount sufficient to effect beneficial or desired clinical results. An effective amount can be administered in one or more administrations. The antibodies, peptides or vectors used as vaccines of the present invention can be administered to a patient at therapeutically effective doses to treat (including prevention) heart disease and/or other muscular contractile disorders. A therapeutically effective dose refers to that amount of the compound sufficient to result in desired treatment. As used herein, the term "antibody or antibodies" includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library. "Antibody" refers to a polypeptide ligand substantially encoded by an immunoglobulin gene or immunoglobulin genes, or fragments thereof, which specifically binds and recognizes an epitope (e.g., an antigen). The recognized immunoglobulin-genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'.sub.2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, CH, CH.sub.2 and CH.sub.3, but does not include the heavy chain variable region.

As used herein, the term "fragment", as applied to an antibody means any fragment of the antibody that includes the antigenic determinant/epitope to which the complete antibody binds, including Fab, Fab', F(ab)$_2$, and F(ab')$_2$ fragments.

As used herein, the term "substantially pure or purified" describes a compound (e.g., a protein or polypeptide) which has been separated from components which naturally accompany it. Typically, a compound is substantially pure when at least 10%, more preferably at least 20%, more preferably at least 50%, more preferably at least 60%, more preferably at least 75%, more preferably at least 90%, and even more preferably at least 99%, of the total material (by volume, by wet or dry weight, or by mole percent or mole fraction) in a sample is the compound of interest. Purity can be measured by any appropriate method. In the case of polypeptides, for example, purity can be measured by column chromatography, polyacrylamide gel electrophoresis, or HPLC analysis. A compound such as a protein is also substantially purified when it is essentially free of naturally associated components or when it is separated from the native contaminants which accompany it in its natural state.

A "substantially pure nucleic acid or purified", as used herein, refers to a nucleic acid sequence, segment, or fragment which has been purified from the sequences which flank it in a naturally occurring state, e.g., a DNA fragment which has been removed from the sequences which are normally adjacent to the fragment such as the sequences adjacent to the fragment in a genome in which it naturally occurs. The term also applies to nucleic acids which have been substantially purified from other components which naturally accompany the nucleic acid, e.g., RNA or DNA, which has been purified from proteins which naturally accompany it in the cell.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. "Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

A "replicon" refers to a polynucleotide comprising an origin of replication which allows for replication of the polynucleotide in an appropriate host cell. Examples include replicons of a target cell into which a heterologous nucleic acid might be integrated (e.g., nuclear and mitochondrial chromosomes), as well as extrachromosomal replicons (such as replicating plasmids and episomes).

In accordance with the invention, the antibodies of the invention are also used as diagnostic agents which detect muscle contractile disorders, especially, for example, in the heart. In one embodiment, any of the above-described molecules can be labeled, either detectably, as with a radioisotope, a paramagnetic atom, a fluorescent moiety, an enzyme, etc. in order to facilitate its detection in, for example, in situ or in vivo assays. The molecules may be labeled with reagents such as biotin, in order to, for example, facilitate their recovery, and/or detection.

As used herein, "inotropic agents" or "inotropic antibodies" will be used interchangeably and refers to the effect such agents produce, i.e. improves cardiac output by increasing the force of myocardial muscle contraction. "Positive inotropic effect" means that the contractility of the cells is enhanced in a dose-dependent manner. A positive inotropic effect-producing amount of antibodies or peptides of the invention can be administered to a "mammalian host" (e.g., a human) to treat cardiac malfunction (e.g., congestive heart failure, paroxysmal atrial tachycardia, atrial fibrillation and flutter). Administration can be either enteral (i.e., oral) or parenteral (e.g., via intravenous, subcutaneous or intramuscular injection).

As used herein, the term "antibody" refers to a polypeptide or group of polypeptides which are comprised of at least one binding domain. An antibody binding domain is formed from the folding of variable domains of an antibody molecule to form three-dimensional binding spaces with an internal surface shape and charge distribution complementary to the features of an antigenic determinant of an antigen. This allows an immunological reaction with the antigen. Antibodies include recombinant proteins comprising the binding domains, as wells as fragments, including Fab, Fab', F(ab)$_2$, and F(ab')$_2$ fragments.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

As used herein, an "antigenic determinant" is the portion of an antigen molecule that determines the specificity of the antigen-antibody reaction. An "epitope" also refers to an antigenic determinant of a polypeptide and is used interchangeably herein. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. Proc. Natl. Acad. Sci. U.S.A. 81:3998-4002; PCT Publication No. WO 84/03564; and PCT Publication No. WO 84/03506.

The phrase "binds" to an antibody or "specific binding" or "selective binding" when referring to a protein or peptide, refers to a binding reaction that is determinative of the presence of the protein in a heterogeneous population of proteins and other biologics. Thus, under designated immunoassay conditions, the specified antibodies or other compounds bind to a particular protein or peptide at least two times the background and do not substantially bind in a significant amount to other proteins or peptides present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Immunoassay" is an assay that uses an antibody to specifically bind an antigen (e.g., a marker). The immunoassay is characterized by the use of specific binding properties of a particular antibody to isolate, target, and/or quantify the antigen.

In another preferred embodiment, where the antibodies or their fragments are intended for therapeutic purposes, it is desirable to "humanize" them in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., International Patent Publication PCT/U.S.86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041-1043 (1988); Liu, A. Y. et al. Proc. Natl. Acad. Sci. USA 84:3439-3443 (1987); Liu, A.Y. et al., J. Immunol. 139:3521-3526 (1987); Sun, L. K. et al., Proc. Natl. Acad. Sci. USA 84:214-218 (1987); Nishimura, Y. et al., Canc. Res. 47:999-1005 (1987); Wood, C. R. et al., Nature 314:446-449 (1985)); Shaw et al., J. Natl. Cancer Inst. 80:1553-1559 (1988); all of which references are incorporated herein by reference). General reviews of "humanized" chimeric antibodies are provided by Morrison, S. L. (Science, 229:1202-1207 (1985)) and by Oi, V. T. et al., BioTechniques 4:214 (1986); which references are incorporated herein by reference).

Suitable "humanized" antibodies can alternatively be produced by CDR or CEA substitution (Jones, P. T. et al., Nature 321:552-525 (1986); Verhoeyan et al., Science 239:1534 (1988); Beidler, C. B. et al., J. Immunol. 141:4053-4060 (1988); all of which references are incorporated herein by reference).

As used herein, the term "humanized" antibody refers to a molecule that has its CDRs (complementarily determining regions) derived from a non-human species immunoglobulin and the remainder of the antibody molecule derived mainly from a human immunoglobulin. The term "antibody" as used herein, unless indicated otherwise, is used broadly to refer to both antibody molecules and a variety of antibody derived molecules. Such antibody derived molecules have at least one variable region (either a heavy chain of light chain variable region) and include molecules such as Fab fragments, Fab' fragments, F(ab')$_2$ fragments, Fd fragments, Fab' fragments, Fd fragments, Fabc fragments, Sc antibodies (single chain antibodies), diabodies, individual antibody light chains, individual antibody heavy chains, chimeric fusions between antibody chains and other molecules, and the like.

The term "variable region" as used herein in reference to immunoglobulin molecules has the ordinary meaning given to the term by the person of ordinary skill in the act of immunology. Both antibody heavy chains and antibody light chains may be divided into a "variable region" and a "constant region". The point of division between a variable region and a heavy region may readily be determined by the person of ordinary skill in the art by reference to standard texts describing antibody structure, e.g., Kabat et al "Sequences of Proteins of Immunological Interest: 5th Edition" U.S. Department of Health and Human Services, U.S. Government Printing Office (1991).

The present invention provides humanized antibody molecules specific for antigenic determinants or epitopes defined by peptides having an amino acid sequence DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), and fragments, derivatives and variants thereof. However, the invention is not limited to these sequences but applies to any sequence in which antibodies can bind resulting in an increase in NKA activity, and in the case of SSA401, in cardiac positive inotropy. In accordance with the present invention, the humanized antibodies are comprised of antigen specific regions in which at least parts of the CDRs of the heavy and/or light chain variable regions of a human antibody (the receptor antibody) have been substituted by analogous parts of CDRs of a murine monoclonal antibody. In a preferred embodiment of the subject invention, the CDR regions of the humanized antibodies are derived from rabbits as described in the examples which follow. Some of the humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitutions that improve the binding properties of a humanized antibody region that is specific for the same target as the NKA activity-increasing antibodies. A minimal number of substitutions are made to the framework region in order to avoid large-scale introductions of non-human framework residues and to ensure minimal immunogenicity of the humanized antibody in humans.

The humanized antibodies compositions of the invention or other therapeutic agents of the invention may be administered to a patient in a variety of ways. In some embodiments the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected. Local injection or infusions can also be used.

Actual methods for preparing parenterally administrable compositions and adjustments necessary for administration to subjects will be known or apparent to those skilled in the art and are described in more detail in, for example, Remington's Pharmaceutical Science, 15th Ed., Mack Publishing Company, Easton, Pa. (1980), which is incorporated herein by reference.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin Remington's Pharm. Sci., 15th Ed. (Mack Publ. Co., Easton (1975)).

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED.50. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the ED50 with little or no toxicity. The dosage can vary within this range depending upon-the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography. A typical daily dose for the therapeutic molecules of the invention (i.e., antibodies, peptides, vectors encoding peptides) of the present invention might range from about 1 microgram/kg to about 100 mg/kg of patient body weight or more per day, depending on the factors mentioned above, preferably about 10 microgram/kg/day to 10 mg/kg/day.

Pharmaceutical compositions for use in accordance with the present invention can be formulated in conventional manner using one or more physiologically acceptable carriers or excipients. Thus, the compounds and their physiologically acceptable salts and solvates can be formulated for administration by intra venous, intranasal or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate. talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

The treatment of heart diseases and contractile disorders can be monitored bin various ways, including echography and electrocardiograms. Echocardiography is the preferred method of monitoring treatment using the molecules of the invention.

The invention also provides for vectors which are used for treating a patient suffering from or susceptible heart disease. As used herein, a "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available (see, e.g., the various references cited below).

As used herein, the term "administering a molecule to a cell" (e.g., an expression vector, nucleic acid, peptide, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell). This term is to be distinguished from administering a composition to a patient.

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10.)

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

A "recombinant viral vector" refers to a viral vector comprising one or more heterologous genes or sequences. Since many viral vectors exhibit size-constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation) (see, e.g., the references and illustrations below). Modified viral vectors in which a polynucleotide to be delivered is carried on the outside of the viral particle have also been described (see, e.g., Curiel, D T, et al. PNAS 88: 8850-8854, 1991).

Viral "packaging" as used herein refers to a series of intracellular events that results in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" genes, found in many viral genomes, are genes encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain genes encoding the missing functions which can be supplied in trans). For example, such packaging genes can be stably integrated into a replicon of the packaging cell line or they can be introduced by transfection with a "packaging plasmid" or helper virus carrying genes encoding the missing functions.

A "detectable marker gene" is a gene that allows cells carrying the gene to be specifically detected (e.g., distinguished from cells which do not carry the marker gene). A large variety of such marker genes are known in the art. Preferred examples thereof include detectable marker genes which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining, as described below.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., WO 92/08796, published May 29, 1992, and WO 94/28143, published Dec. 8, 1994). Such marker genes can provide an added measure of control that can be advantageous in gene therapy contexts. "Treatment" or "therapy" as used herein also refers to administering, to an individual patient, agents that are capable of eliciting a prophylactic, curative or other beneficial effect in the individual.

"Gene therapy" as used herein refers to administering, to an individual patient, vectors comprising a therapeutic gene, such as the vectors carrying one or more of the peptides DVEDSYGQQWTYEQR (SEQ ID: 5), RSATEEEPPNDD (SEQ ID: 3), KRQPRNPKTDKLVNE (SEQ ID: 1), VPAISLAYEQAESD (SEQ ID: 2) and HLLGIRETWDDRWIN (SEQ ID: 4), or to fragments, derivatives or variants thereof.

A "therapeutic polynucleotide" or "therapeutic gene" refers to a nucleotide sequence that is capable, when transferred to an individual, of eliciting a prophylactic, curative or other beneficial effect in the individual. Such as expressing one or more of the peptide antigenic epitopes described herein which in turn elicit an immune response from the host.

The practice of the present invention can suitably employ, unless otherwise indicated, conventional techniques of molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W.B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

Preferred vectors for use in the present invention include viral vectors, lipid-based vectors and other vectors that are capable of delivering DNA to non-dividing cells in vivo. Presently preferred are viral vectors, particularly replication-defective viral vectors (including, for example replication-defective adenovirus vectors and adeno-associated virus (AAV) vectors. For ease of production and use in the present invention, replication-defective adenovirus vectors are presently most preferred.

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein. Targeted vectors include vectors (such as viruses, non-viral protein-based vectors and lipid-based vectors) in which delivery results in transgene expression that is relatively limited to particular host cells or host cell types. By way of illustration, therapeutic molecules, for example, nucleic acid sequences encoding for the peptides of the invention, to be delivered to a patient can be operably linked to heterologous tissue-specific promoters thereby restricting expression to cells in that particular tissue.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

When vectors are used to express peptide epitopes for example to stimulate production of antibody for use in treating or preventing diseases associated with low NKA activity, including heart disease or contractile disorders, they are sometimes administered systemically. Other times they are administered locally for example by injection into a blood vessel directly supplying the target tissue. For example, if it is the heart, then they are injected into a vessel supplying the myocardium, preferably by injection into a coronary artery. Such injection is preferably achieved by catheter introduced substantially (typically at least about 1 cm) within the ostium of one or both coronary arteries or one or more saphenous veins or internal mammary artery grafts or other conduits delivering blood to the myocardium. By injecting the vector stock, preferably containing no wild-type virus, deeply into the lumen of an artery (or grafts and other vascular conduits), and preferably in an amount of about $10^{7-13}$ viral particles as determined by optical densitometry (more preferably $10^{9-11}$ viral particles), it is possible to locally transfect a desired number of cells with genes that encode proteins that regulate cell NKA activity, such as, for example, the peptides discussed herein. This maximizes the therapeutic efficacy of gene transfer, and minimizes undesirable effects at other sites such as the possibility of an inflammatory response to viral proteins. For example, vector constructs that are specifically targeted to the myocardium, such as vectors incorporating myocardial-specific binding or uptake components, and/or which incorporate inotropic molecules, for example, the peptides described above, that are under the control of myocardial-specific transcriptional regulatory sequences (e.g., ventricular myocyte-specific promoters) can be used in place of or, preferably, in addition to such directed injection techniques as a means of further restricting expression to the myocardium, especially the ventricular myocytes. For vectors that can elicit an immune response, it is preferable to inject the vector directly into a blood vessel supplying the targeted cells or tissue, although the additional techniques for restricting the potential for non-target expression can also be employed.

The invention also provides for methods for identifying peptides and antibodies that activate NKA and therefore come within the scope of the invention. To prepare an antibody that specifically binds to a region of the NKA, purified peptides or their nucleic acid sequences representing the different subunits of NKA can be used. Using these purified peptides or their nucleic acid sequences, antibodies that specifically bind to a desired peptide can be prepared using any suitable method known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing animals (see, e.g., Huse et al, Science 246:1275-1281 (1989); Ward et al., Nature 341:544-546 (1989)); humanized antibodies; production of antibodies by any of the methods discussed above. After the antibody is provided, the specificity of the antibody can be detected using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Ten, eds., 7th ed. 1991); and Harlow & Lane, supra.

To determine whether these identified antibodies increase NKA activity or are positive inotropic agents, standard assays such as those described in the Examples which follow can be used. For example, measurement of cell contraction assays; confocal Ca ion imaging; NKA activity assays and the like.

EXAMPLES

Example 1

Preparation of Antibodies

Polyclonal antibodies SSA78, 95, 97, 401 and 412 were generated against NKA in New Zealand white rabbits using KLH (Keyhole Limpet Hemocyanin) as a peptide carrier. Sprague Dawley rats were obtained from Charles River Laboratories. Protocols were approved by the Animal Care and Use Committees of the University Of Maryland School Of Medicine. The peptides were synthesized according to the protein sequence reported (Schneider, J. W., Mercer, R. W., Caplan, M., Emanuel, J. R., Sweadner, K. J., Benz, E. J., Levenson, R. (1985) Proc. Natl. Acad. Sci. U.S.A. 82, 6357-6361; Xie, Z., Li, H., Liu, G., Wang, Y., Askari, A., Mercer, R. W. (1994) Cloning of the dog Na/K-ATPase alpha 1-subunit. The Na Pump. (Bamberg, S., and Schoner, W., Eds), pp. 49-52, Springer-Verlag, New York, N.Y.; Shull, M. M., Lingrel, J. B. (1987) Proc. Natl. Acad. Sci. U.S.A. 84, 4039-4043). The immunoglobulins (IgG) were purified through an affinity column directed against the same synthetic peptide of the NKA. Purified antibodies against peptide epitopes in NKATPase recognize both denatured (by Western blots) and native NKATPase (by immunocytostaining). Synthetic peptide was also utilized as the specific peptide blockers for the antibodies.

Example 2

Isolation of Cardiac Myocytes

Ventricular cardiac myocytes were isolated from adult Sprague-Dawley rats (2-3 months old, weight 225-300 g) using standard enzymatic technique as described previously.[1] Briefly, following anaesthesia (sodium pentobarbital, 100 mg/kg), the heart was quickly removed from the chest and aortic perfused at constant pressure at 37° C. for 3 min with a $Ca^{2+}$-free bicarbonate-based buffer containing 120 mM NaCL, 5.4 mM $MgSO_4$, 1.2 mM $NaH_2PO_4$, 5.6 mM glucose, 20 mM $NaHCO_3$, and 5 mM taurine, in the presence of $O_2$ (95%)/$CO_2$ (5%). Enzymatic digestion was initiated by adding collagenase (Worthington Type II, 1 mg/ml) to the perfusion solution. Calcium (50 µM) was added to the enzyme solution when the heart became swollen. About 7 min later, the left ventricle was quickly removed, cut into several pieces, and further digested on a shaker (60-70 rpm) for 10 min in the same enzyme solution. The supernatant containing the dispersed myocytes was filtered into a test tube and gently centrifuged at 500 rpm for 1 min. The cell pellet was then promptly resuspended in a solution containing 0.125 mM $Ca^{2+}$. The supernatant was aspirated after the myocytes were pelleted by gravity for 10 min, and the myocytes were resuspended in a solution containing 0.25 mM $Ca^{2+}$. The shake-harvest procedure was repeated several times until all the pieces were digested. For freshly isolated cells, myocytes were suspended in HEPES-buffer consisting of 1 mM $CaCL_2$, 0.137 mM NaCL, 5.4 mM KCL, 15 mM dextrose, 1.3 mM $MgSO_4$, 1.2 mM $NaH_2PO_4$, and 20 mM HEPES, pH 7.4.

Example 3

Measurement of Cell Contraction (Cell Shortening)

Myocytes were placed on an inverted microscope (Zeiss model IM-35), superfused with HEPES-buffered solution at a flow rate of 1.8 ml/min, and electrically stimulated at 0.5 Hz at 23° C. Cell length was monitored from the bright-field image (650 nm to 750 nm red light illumination) by an optical edge-tracking method using a photodiode array (model 1024 SAQ, Reticon) with a 3-ms time resolution. Contraction amplitude was measured as the percentage of shortening of cell length.

Example 4

Immunoprecipitation, Blotting, and Immunofluorescent Staining

Isolated rat heart cells were incubated in 1 ml cold lysis buffer containing 150 mM NaCl, 10 mM EDTA, 1% NP-40, 1 mM $Na_3VO_4$, and 1× protease inhibitor cocktail as described [12], with or without antibody. Immunoprecipitates were boiled for 5 min and loaded on a 7% SDS gel, and transferred from the SDS gel to a nitrocellulose membrane.

The nitrocellulose membrane was blocked with 5% nonfat milk for 1 hour and incubated with SSA412 or other control antibodies overnight at 4° C. Alkaline phosphatase conjugated secondary antibody (1:2500) was then incubated with the membrane for 1 hour and washed 3 times with TBS in 0.05% Tween-20. Color was developed using a reagent containing a mixture of NBT and BCIP (Promega Corporation, WI). For immunofluorescent staining, rat myocytes were frozen and cut on a cryostat. Sections (8 μm) of each tissue were blocked with 1% bovine serum albumin (BSA) and incubated with SSA412 (1:100) for 60 min in the presence or absence of 5, 10, and 20 mM ouabain. Washed slides were evaluated after incubation with a FITC conjugated goat anti-rabbit antibody (1:75).

Example 5

Intracellular $Ca^{2+}$ Transients and Cell Contraction

Cardiac myocytes were isolated from adult Sprague-Dawley rats, using standard enzymatic methods [13], and suspended in buffer containing (in mM) 137 NaCl, 5.4 KCl, 15 dextrose, 1.3 $MgSO_4$, 1.2 $NaH_2PO_4$, 1 $CaCl_2$, and 20 HEPES, pH 7.4. Myocytes were loaded with 50 μs of Indo-1/AM for 10 min, washed and resuspended in HEPES-buffered solution in the presence of 1 mM $Ca^{2+}$, then stored in the dark at room temperature (RT) for 60 min before use [14]. Cells were placed on the stage of a modified inverted microscope equipped for simultaneous recording of both Indo-1 fluorescence and cell length. Cells were studied at room temperature at a stimulation rate of 0.5 Hz, excited at 350-nm, and the ratio of 410:490 emission was determined to quantify intracellular calcium. Cells were electrically stimulated at 0.5 Hz at 25° C. and monitored by optical edge-tracking using photodiode array. Contraction amplitude was indexed by the percent shortening of cell length.

Example 6

Isolation of Sarcolemmal Vesicles and Purification of NKA

Cardiac sarcolemmal (SL) vesicles were isolated from rat hearts as reported previously [15]. The SL vesicles were tested with saponin and found to be predominately right-side-out in orientation. NKA was further purified as described [16]. Briefly, rat SL vesicles (4.4 mg/ml) were titrated with 0.58 mg/ml of SDS in the presence of 2 mM ATP at 20° C. for 30 min and then loaded on the top of a sucrose (W/W) step gradient (15%, 28.8% & 37.3%) in a Ti 60 tube and centrifuged at 40,000 rpm for 90 minutes. The fractions that contain NKA were collected and stored at −70° C.

Example 7

Enzyme Catalytic Activity

NKA activity was determined based on Jack Kyte's method as previously described [17] under various experimental conditions as indicated in FIG. 2. All NKA activities in different experiments are ouabain-sensitive activity. Purified ouabain-resistant rat NKA and ouabain-sensitive dog NKA were used to verify the data. Enzymes were incubated with or without SSA412 for 60 min at room temperature. The reaction was initiated by adding different concentrations of MgATP in a final volume of 0.25 ml at 37° C. for 30 min and terminated by adding 0.75 ml quench solution and 0.025 ml developer. Color was developed for 30 minutes at room temperature and the concentration of phosphate was then determined at 700 nm using a spectrophotometer. NKA turnover number ($k_{cat}$) was calculated using the equation $k_{cat}=V_{max}/E_t$, where $V_{max}$ is the maximal velocity (rate of reaction) and $E_t$ represents enzyme concentration.

Example 8

Enzyme Phosphorylation

Purified rat or dog NKA was phosphorylated in 20 mM Tris/Cl buffer (pH 7.4) in the presence of 100 mM $Na^+$ without $K^+$ or 20 mM $K^+$ without $Na^+$, 10 μM MgATP, and 1 nM [γ-$^{32}$P]ATP (3000 Ci/mmol) with or without SSA412 or total rabbit IgG. The reaction was stopped at the end of the indicated time interval by a quench solution at pH 2.0. Samples were transferred to a 2.0 ml polypropylene tube with 0.45 μm cellulose acetate filter and washed three times. The radioactivity of each sample was determined using a β-scintillation counter. The number of net $^{32}$P bound to the enzyme was calculated and compared with control samples in the presence of SSA412.

Example 9

Measuring L-Type $Ca^{2+}$ Currents and Myoplasmic $Ca^{2+}$ Transients in Rat Neonatal Ventricular Myocytes The effects of SSA412 antibody on L-type $Ca^{2+}$ currents and myoplasmic $Ca^{2+}$ transients were measured in rat neonatal ventricular myocytes grown on cover slips and voltage-clamped ('whole-cell' patch-clamp). Myoplasmic $Ca^{2+}$ was determined from simultaneous confocal optical recording of fluo-4 fluorescence. FIG. 9 The left-hand column represents a control myocyte, while the right-hand column shows results from a myocyte previously exposed to SSA412 antibody (1.0 uM). FIG. 9A The voltage pulse protocol, $V_M$. A ramp preceded each test pulse (−10 mV, 100 ms) in order to suppress $Na^+$ and T-type $Ca^{2+}$ currents. FIG. 9B LTCC currents ($I_{Ca}$), corrected for linear capacitance and leak using a P/4 protocol. FIG. 9C Myoplasmic $Ca^{2+}$ during and after the test pulse. Panel C shows the myoplasmic $Ca^{2+}$ as determined from confocal line-scan (x vs. t) images. FIG. 9D Averaged results of peak $I_{Ca}$ and peak myoplasmic $Ca^{2+}$ elevation in each group. Values represent the mean (±SEM).

Example 10

Cyclic AMP Assays

Isolated rat cardiac myocytes were treated without or with the phosphodiesterase inhibitor 3-isobutyl-1-methylxanthine (IBMX, 1 mM) as shown in FIG. 11 side by side for 30 min at room temperature prior to being incubated with either active SSA412 antibody or boiled SSA412 (4 μM each) for 30 min, or with b-AR agonist, isoprotenol (1 mM) for 5 min as a positive control. Formation of cAMP was assayed using $^3$H-cAMP assay kit obtained from Amersham (Arlington Heights, Ill.). Protein concentration was measured using the Bradford method (Bio-Rad, Richmond, Calif.) with bovine serum albumin as standard. a a': control samples; b and b': with 1 micromolar isoprotenol; c and c': with denatured SSA412; d and d': with active SSA412; a', b', c' and d': in the presence of 1 mM IBMX.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

REFERENCES

[1] J. C. Skou, Nobel Lecture. The identification of the sodium pump, Biosci Rep 18 (1998) 155-169.
[2] J. Kyte, Molecular considerations relevant to the mechanism of active transport, Nature 292 (1981) 201-204.
[3] G. E. Shull, A. Schwartz, and J. B. Lingrel, Amino-acid sequence of the catalytic subunit of the $(Na^++K^+)$ATPase deduced from a complementary DNA, Nature 316 (1985) 691-695.
[4] J. B. Lingrel, J. M. Arguello, J. Van Huysse, and T. A. Kuntzweiler, Cation and cardiac glycoside binding sites of the Na,K-ATPase, Ann N Y Acad Sci 834 (1997) 194-206.
[5] J. H. Kaplan, Biochemistry of Na,K-ATPase, Annu Rev Biochem 71 (2002) 511-535.
[6] G. E. Shull, L. K. Lane, and J. B. Lingrel, Amino-acid sequence of the beta-subunit of the $(Na^++K^+)$ATPase deduced from a cDNA, Nature 321 (1986) 429-431.
[7] K. J. Sweadner, Isozymes of the $Na^+/K^+$-ATPase, Biochim Biophys Acta 988 (1989) 185-220.
[8] P. A. Lucchesi, and K. J. Sweadner, Postnatal changes in Na,K-ATPase isoform expression in rat cardiac ventricle. Conservation of biphasic ouabain affinity, J Biol Chem 266 (1991) 9327-9331.
[9] A. A. McDonough, Y. Zhang, V. Shin, and J. S. Frank, Subcellular distribution of sodium pump isoform subunits in mammalian cardiac myocytes, Am J Physiol 270 (1996) C1221-1227.
[10] A. A. McDonough, J. B. Velotta, R. H. Schwinger, K. D. Philipson, and R. A. Farley, The cardiac sodium pump: structure and function, Basic Res Cardiol 97 Suppl 1 (2002) I19-24.
[11] J. Wang, J. B. Velotta, A. A. McDonough, and R. A. Farley, All human Na(+)-K(+)-ATPase alpha-subunit isoforms have a similar affinity for cardiac glycosides, Am J Physiol Cell Physiol 281 (2001) C1336-1343.
[12] K. Y. Xu, E. Takimoto, G. J. Juang, Q. Zhang, H. Rohde, and A. C. Myers, Evidence that the H1-H2 domain of alpha1 subunit of $(Na^++K^+)$-ATPase participates in the regulation of cardiac contraction, Faseb J 19 (2005) 53-61.
[13] S. Q. Wang, L. S. Song, E. G. Lakatta, and H. Cheng, Ca2+ signalling between single L-type $Ca^{2+}$ channels and ryanodine receptors in heart cells, Nature 410 (2001) 592-596.
[14] S. H. Jo, V. Leblais, P. H. Wang, M. T. Crow, and R. P. Xiao, Phosphatidylinositol 3-kinase functionally compartmentalizes the concurrent G(s) signaling during beta2-adrenergic stimulation, Circ Res 91 (2002) 46-53.
[15] L. R. Jones, Rapid preparation of canine cardiac sarcolemmal vesicles by sucrose flotation, Methods Enzymol 157 (1988) 85-91.
[16] J. Kyte, Purification of the sodium- and potassium-dependent adenosine triphosphatase from canine renal medulla, J Biol Chem 246 (1971) 4157-4165.
[17] J. Kyte, K. Y. Xu, and R. Bayer, Demonstration that lysine-501 of the alpha polypeptide of native sodium and potassium ion activated adenosinetriphosphatase is located on its cytoplasmic surface, Biochemistry 26 (1987) 8350-8360.
[18] J. W. Schneider, R. W. Mercer, M. Caplan, J. R. Emanuel, K. J. Sweadner, E. J. Benz, Jr., and R. Levenson, Molecular cloning of rat brain Na,K-ATPase alpha-subunit cDNA, Proc Natl Acad Sci USA 82 (1985) 6357-6361.
[19] G. E. Shull, J. Greeb, and J. B. Lingrel, Molecular cloning of three distinct forms of the $Na^+,K^+$-ATPase alpha-subunit from rat brain, Biochemistry 25 (1986) 8125-8132.
[20] M. M. Shull, and J. B. Lingrel, Multiple genes encode the human $Na^+,K^+$-ATPase catalytic subunit, Proc Natl Acad Sci USA 84 (1987) 4039-4043.
[21] L. H. Xie Z, Liu G, Wang Y, Askari A, Mercer R W., Cloning of the dog Na,K-ATPase alpha 1 subunit., ed., Springer-Verlag, New York 1994.
[22] A. Ovchinnikov Yu, N. N. Modyanov, N. E. Broude, K. E. Petrukhin, A. V. Grishin, N. M. Arzamazova, N. A. Aldanova, G. S. Monastyrskaya, and E. D. Sverdlov, Pig kidney $Na^+,K^+$-ATPase. Primary structure and spatial organization, FEBS Lett 201 (1986) 237-245.
[23] M. M. Shull, D. G. Pugh, and J. B. Lingrel, Characterization of the human Na,K-ATPase alpha 2 gene and identification of intragenic restriction fragment length polymorphisms, J Biol Chem 264 (1989) 17532-17543.
[24] A. Ovchinnikov Yu, G. S. Monastyrskaya, N. E. Broude, A. Ushkaryov Yu, A. M. Melkov, V. Smimov Yu, I. V. Malyshev, R. L. Allikmets, M. B. Kostina, I. E. Dulubova, and et al., Family of human $Na^+$, $K^+$-ATPase genes. Structure of the gene for the catalytic subunit (alpha III-form) and its relationship with structural features of the protein, FEBS Lett 233 (1988) 87-94.
[25] J. C. Skou, The Na,K-pump, Methods Enzymol 156 (1988) 1-25.
[26] D. G. Allen, D. A. Eisner, and S. C. Wray, Birthday present for digitalis, Nature 316 (1985) 674-675.
[27] B. Forbush, 3rd, and J. F. Hoffman, Evidence that ouabain binds to the same large polypeptide chain of dimeric Na,K-ATPase that is phosphorylated from Pi, Biochemistry 18 (1979) 2308-2315.
[28] I. M. Glynn, The Action Of Cardiac Glycosides On Ion Movements, Pharmacol Rev 16 (1964) 381-407.
[29] J. C. Skou, Enzymatic Basis For Active Transport Of $Na^+$ And $K^+$ Across Cell Membrane, Physiol Rev 45 (1965) 596-617.
[30] T. W. Smith, Digitalis. Mechanisms of action and clinical use, N Engl J Med 318 (1988) 358-365.
[31] K. Xu, et al. Site-specific Antibody of $(Na^++K^+)$-ATPase Augments Cardiac Myocyte Contraction without Inactivating Enzyme Activity; Biochem, biophys. Res. Commun. (2001)289:167-172.
[32] K. Y. Xu. Activation of Na,K-ATPase. Biochem. Biophys. Res. Commun. 338, 1669-1677 (2005).
[32] G. Liguri, et al. Changes in Na+,K(+)-ATPase, Ca2(+)-ATPase and some soluble enzymes related to energy metabolism in brains of patients with Alzheimer's disease. Neurosci Lett. 1990 May 4; 112(2-3):338-42.
[33] C. Kairane, et al. Regulation of the frontocortical sodium pump by Na+ in Alzheimer's disease: difference from the age-matched control but similarity to the rat model FEBS Lett. 2002 Nov. 6; 531(2):241-4.
[34] N. Hattori, et al. CI-ATPase and Na+/K(+)-ATPase activities in Alzheimer's disease brains. Neurosci Lett. 1998 Oct. 2; 254(3):141-4.
[35] C. Scavone, et al. Age-related changes in cyclic GMP and PKG-stimulated cerebellar Na,K-ATPase activity. Neurobiol Aging. 2005 June; 26(6):907-16.
[36] R. Efendiev, et al. Hypertension-linked mutation in the adducin alpha-subunit leads to higher AP2-mu2 phosphorylation and impaired Na+,K+-ATPase trafficking in

[37] Lechi C, et al. Measurement by bioluminescence technique of erythrocyte membrane Na,K-ATPase activity in hypertensive patients. Clin Chim Acta 163:329-337, 1987.
[38] Mattiasson I, et al. Insulin resistance and Na/K-ATPase in hypertensive women: a difference in mechanism depending on the level of glucose tolerance. Clin Sci (Lond) 82:105-111, 1992.
[39] Martinez F J, et al. Epidemiology of high blood pressure and obesity. Drugs 46:160-164, 1993.
[40] Rabini R A, et al: Diabetes mellitus and subjects' ageing: a study on the ATP content and ATP-related enzyme activities in human erythrocytes. Eur J Clin Invest 27:327-332, 1997.
[41] Scarpini E, et al. Decrease of nerve Na,K-ATPase activity in the pathogenesis of human diabetic neuropathy. J Neurol Sci 120:159-167, 1993.
[42] Mimura M, et al. Reduction of erythrocyte (Na,K)-ATPase activity in type 2 (non insulin dependent) diabetic patients with microalbuminuria. Horm Metab Res 26:33-38, 1994.
[43] Rabini R A, et al. Diabetes mellitus and subjects' ageing: a study on the ATP content and ATP-related enzyme activities in human erythrocytes. Eur J Clin Invest 27:327-332, 1997.
[44] Okegbile E O, et al. Erythrocyte membrane digoxin-sensitive (Na,K)-ATPase of non-insulin dependent diabetic humans. Biosci Rep 17:499-506, 1997.
[45] De La Tour D D, et al. Erythrocyte Na/K ATPase activity and diabetes: relationship with C-peptide level. Diabetologia. 1998 September; 41(9):1080-1084.
[46] De La Tour D D, et al. Erythrocyte Na/K ATPase activity and diabetes: relationship with C-peptide level. Diabetologia. 1998 September; 41(9):1080-1084.
[47] Factor P. Role and regulation of lung Na,K-ATPase. Cell Mol Biol (Noisy-le-grand). 2001 March; 47(2):347-61.
[48] Magro F., et al. Regional intestinal adaptations in Na+,K+-ATPase in experimental colitis and the contrasting effects of interferon-gamma. Acta Physiol Scand. 2005 February; 183(2):191-9.
[49] Kurup R. K., et al. The isoprenoid pathway and the pathogenesis of Reye's syndrome. Pediatr Pathol Mol Med. 2003 September-October; 22(5):423-34.
[50] Jonassen T E, et al. Collecting duct function in liver cirrhotic rats with early sodium retention. Acta Physiol Scand. 2002 July; 175(3):237-44.
[51] Rajasekaran S. A., et al. Multiple functions of Na,K-ATPase in epithelial cells. Semin Nephrol. 2005 September; 25(5):328-34.
[52] Li C, et al. Alpha-MSH prevents impairment in renal function and dysregulation of AQPs and Na—K-ATPase in rats with bilateral ureteral obstruction. Am J Physiol Renal Physiol. 2006 February; 290(2):F384-96. Epub 2005 Sep. 27
[53] Greig E, et al. Diarrhea in ulcerative colitis. The role of altered colonic sodium transport. Ann N Y Acad Sci. 2000; 915:327-32.
[54] Wild G. E., et al. Na(+)-K(+)-ATPase alpha 1- and beta 1-mRNA and protein levels in rat small intestine in experimental ileitis. Am J Physiol. 1995 November; 269(5 Pt 1):G666-75.
[55] Darlington D. N., et al. Adenosine stimulates NA/K ATPase and prolongs survival in hemorrhagic shock J Trauma. 2005 January; 58(1):1-6.
[56] Ohta Y., et al. Partial reversal of methylprednisolone-induced opacity in isolated rat lenses. Ophthalmic Res. 2002 May-June; 34(3):128-34.
[57] Tseng S. H., et al. Na,K-ATPase in lens epithelia from patients with senile cataracts. J Formos Med Assoc. 1999 September; 98(9):627-32.
[58] Yagihashi S., et al. Perspective for the treatment of diabetic neuropathy: translation from molecular studies to bedside Rinsho Shinkeigaku. 2005 November; 45(11):966-8.
[59] Capendeguy O, Functional effects of Na+,K+-ATPase gene mutations linked to familial hemiplegic migraine. Neuromolecular Med. 2004; 6(2-3):105-16.
[60] de Vasconcellos A. P., et al. Na+,K(+)-ATPase activity is reduced in hippocampus of rats submitted to an experimental model of depression: effect of chronic lithium treatment and possible involvement in learning deficits. Neurobiol Learn Mem. 2005 September; 84(2):102-10.
[61] Okegbile E O, et al. Erythrocyte membrane digoxin-sensitive (Na,K)-ATPase of non insulin dependent diabetic humans. Biosci Rep 17:499-506, 1997.

The invention claimed is:

1. A method of producing a positive inotropic effect in a mammalian host comprising administering to said mammalian host a therapeutically effective amount of an antibody which binds $(Na^+ + K^+)$-ATPase to increase intracellular calcium; wherein said antibody binds to a peptide consisting of the amino acid sequence as set forth in HLLGIRETWDDRWIN (SEQ ID: 4).

2. The method of claim 1, wherein said antibody is a polyclonal antibody, monoclonal antibody, human or humanized antibody or single chain antibody of the above.

3. The method of claim 1, wherein said antibody is IgA, IgG, IgE, IgD or IgM or a single chain antibody.

4. The method of claim 1, wherein said antibody comprises a fragment selected from the group consisting of Fab, Fab', $F(ab)_2$, and $F(ab')_2$ fragments.

5. The method of claim 1, wherein said antibody is administered in a daily dose of about 1 pg/kg body weight to about 100 mg/kg body weight or more.

6. The method of claim 1, further comprising monitoring the mammalian host's cardiac contractions for a positive inotropic effect.

* * * * *